United States Patent
Moder et al.

[11] Patent Number: 5,986,165
[45] Date of Patent: *Nov. 16, 1999

[54] C-WRAPPED ABSORBENT PAD ARTICLE AND METHOD

[75] Inventors: Susan J. Moder; Richard W. Kubalek, both of Appleton, Wis.

[73] Assignee: Kimberly-Clark Worldwide, Inc., Neenah, Wis.

[*] Notice: This patent is subject to a terminal disclaimer.

[21] Appl. No.: 09/178,161

[22] Filed: Oct. 23, 1998

Related U.S. Application Data

[63] Continuation-in-part of application No. 08/993,024, Dec. 18, 1997, Pat. No. 5,891,127, and a continuation-in-part of application No. 08/993,025, Dec. 18, 1997, Pat. No. 5,827,251.

[51] Int. Cl.⁶ .......................... A61F 13/15; B65D 69/00; A61B 17/06; A45D 40/00
[52] U.S. Cl. .......................... 604/358; 604/904; 206/225; 206/226; 206/438; 206/581; 132/286
[58] Field of Search ...................................... 604/358, 904; 206/225, 226, 438, 440, 570, 574, 581; 132/286

[56] References Cited

U.S. PATENT DOCUMENTS

| | | |
|---|---|---|
| 2,092,346 | 9/1937 | Arone . |
| 4,425,130 | 1/1984 | DesMarais . |
| 4,834,737 | 5/1989 | Khan . |
| 4,848,572 | 7/1989 | Herrera . |
| 5,046,620 | 9/1991 | Barabino ................................ 206/581 |
| 5,117,981 | 6/1992 | Crawford et al. ....................... 206/570 |
| 5,138,457 | 8/1992 | Kadel ....................................... 206/438 |
| 5,180,059 | 1/1993 | Shimatani et al. ....................... 206/440 |
| 5,350,067 | 9/1994 | Beltran . |
| 5,383,868 | 1/1995 | Hyun . |
| 5,429,627 | 7/1995 | Johnson et al. . |
| 5,579,916 | 12/1996 | Manko .................................... 206/581 |
| 5,618,282 | 4/1997 | Schlangen . |
| 5,827,251 | 10/1998 | Moder et al. ............................ 604/358 |

*Primary Examiner*—John G. Weiss
*Assistant Examiner*—Dennis Ruhl
*Attorney, Agent, or Firm*—Thomas J. Connelly; Thomas M. Parker; Douglas G. Glantz

[57] ABSTRACT

Feminine sanitary protection packaging is disclosed which includes a combination vaginal insert or insert applicator and an absorbent pad of a sanitary napkin or panty liner configured to fit the pudendal region of a woman. In one aspect, the panty liner or an ultrathin pad is longitudinally C-wrapped to form a C-wrapped combination panty liner or ultrathin pad and vaginal insert or insert applicator. A pouch is positioned around the longitudinally C-wrapped combination. The pouch provides a means for transporting and disposing of the combination packaging. In one aspect, the vaginal insert includes a tampon or a vaginal suppository. In another aspect, the vaginal insert applicator includes a tampon applicator or a vaginal suppository applicator. In one aspect, the sanitary napkin includes an ultrathin pad or maxipad. In still another aspect, the pouch is sealed and optionally can be perforated on at least one closed end for ease in opening. The pouch can be formed from the release strip of the sanitary napkin or the panty liner and can be used to seal the longitudinally C-wrapped combination.

20 Claims, 11 Drawing Sheets

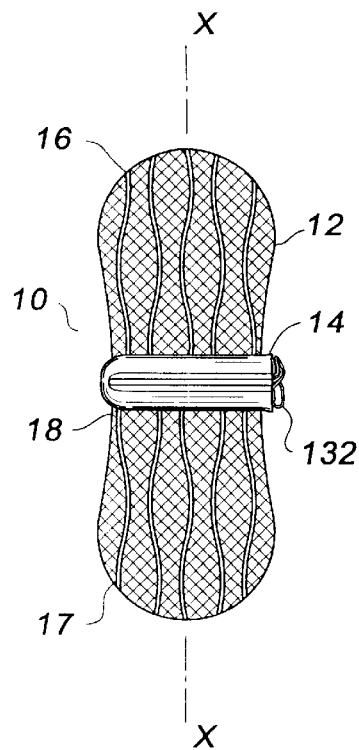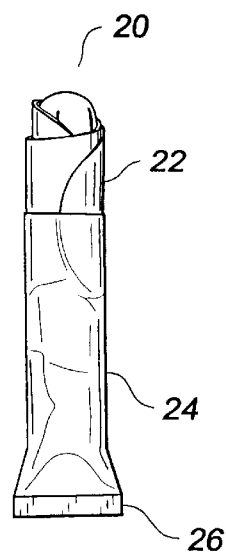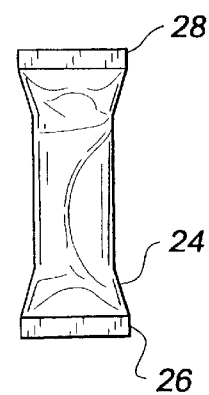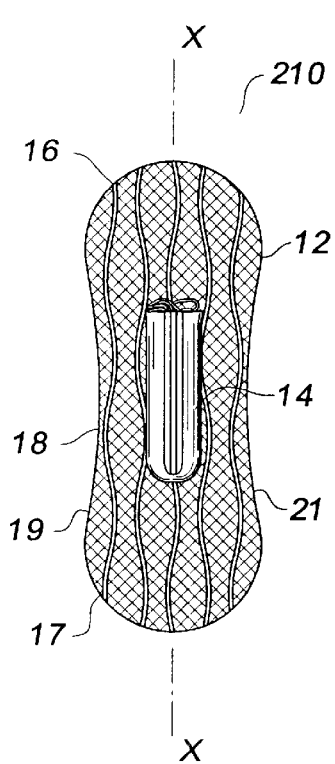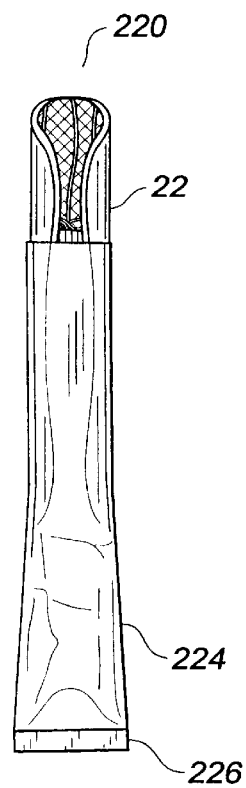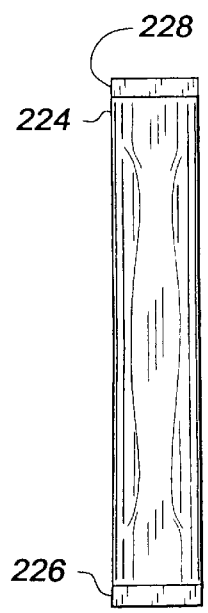
Fig. 1   Fig. 2   Fig. 3
Fig. 4   Fig. 5   Fig. 6

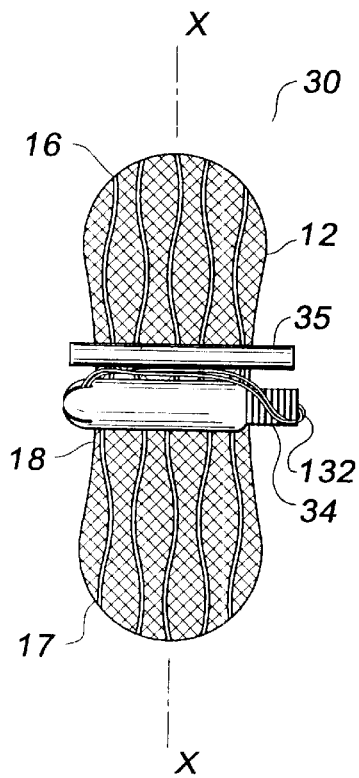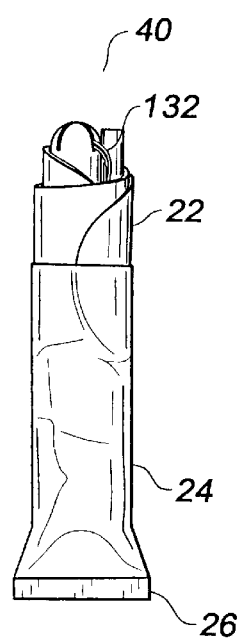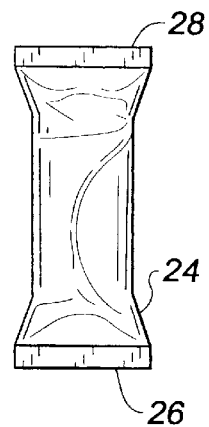
Fig. 7   Fig. 8   Fig. 9
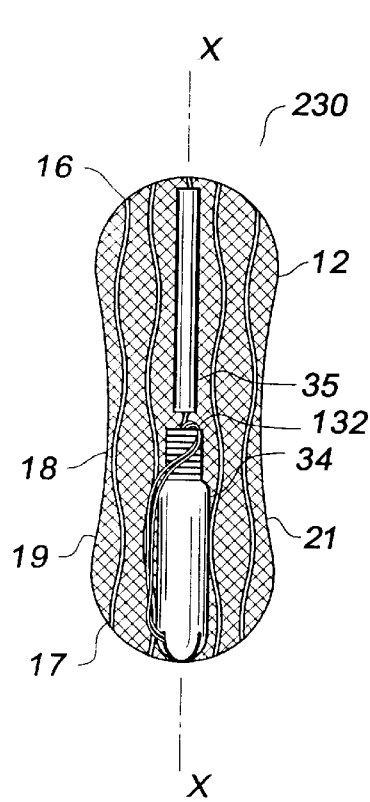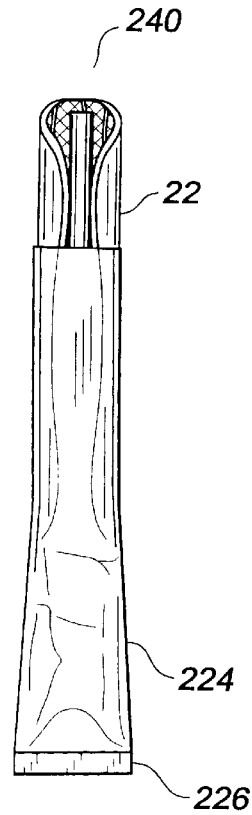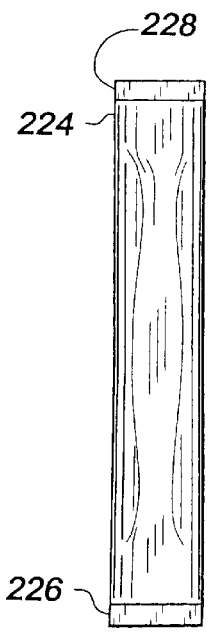
Fig. 10   Fig. 11   Fig. 12

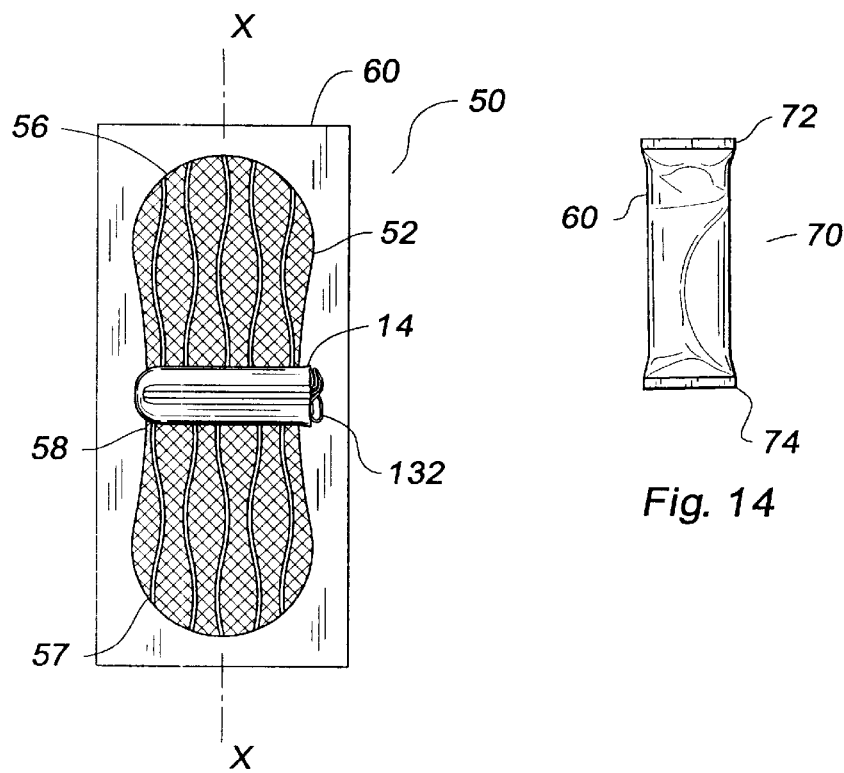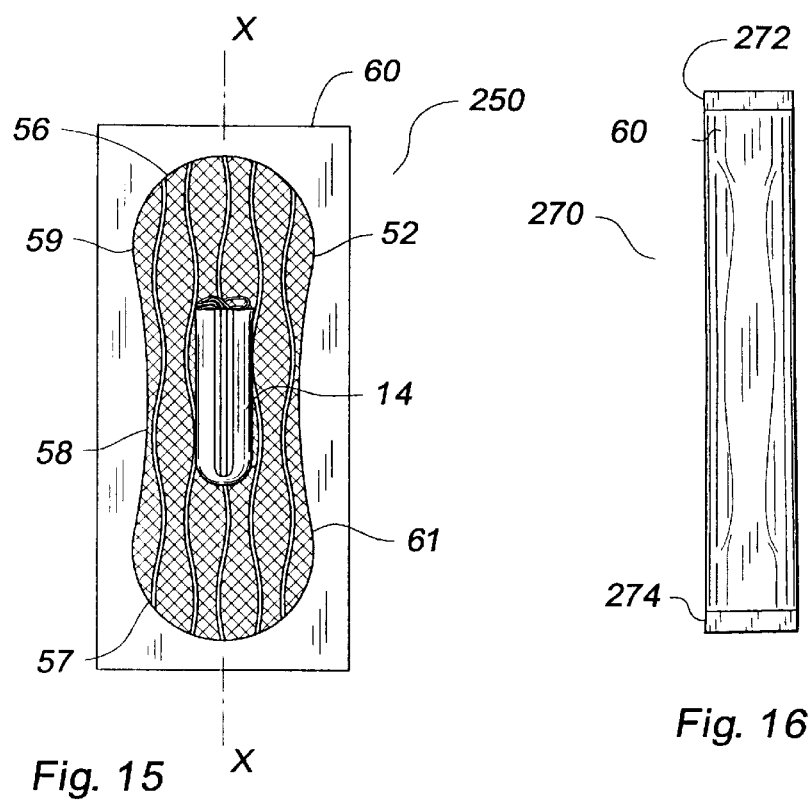

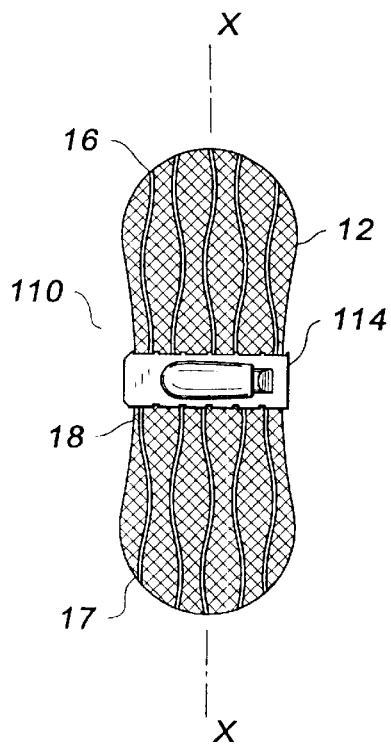
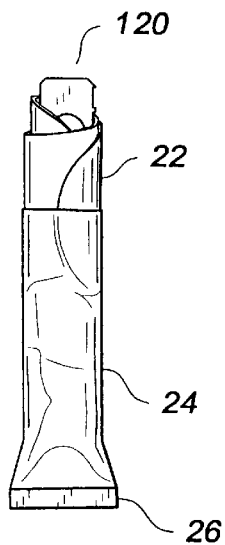
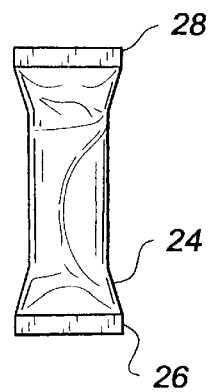
Fig. 21  Fig. 22  Fig. 23
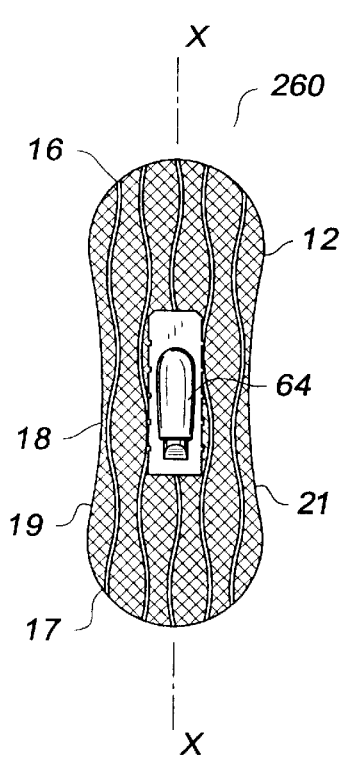
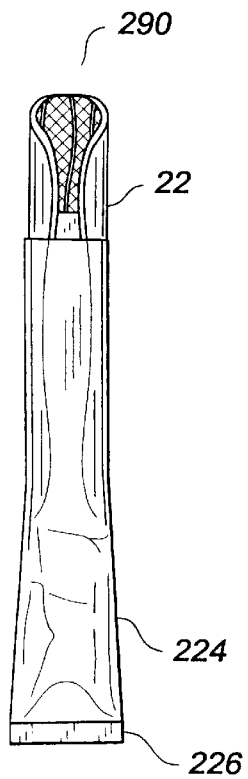
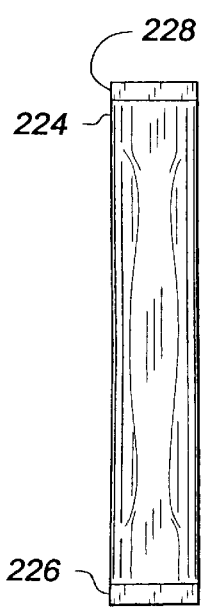
Fig. 24  Fig. 25  Fig. 26

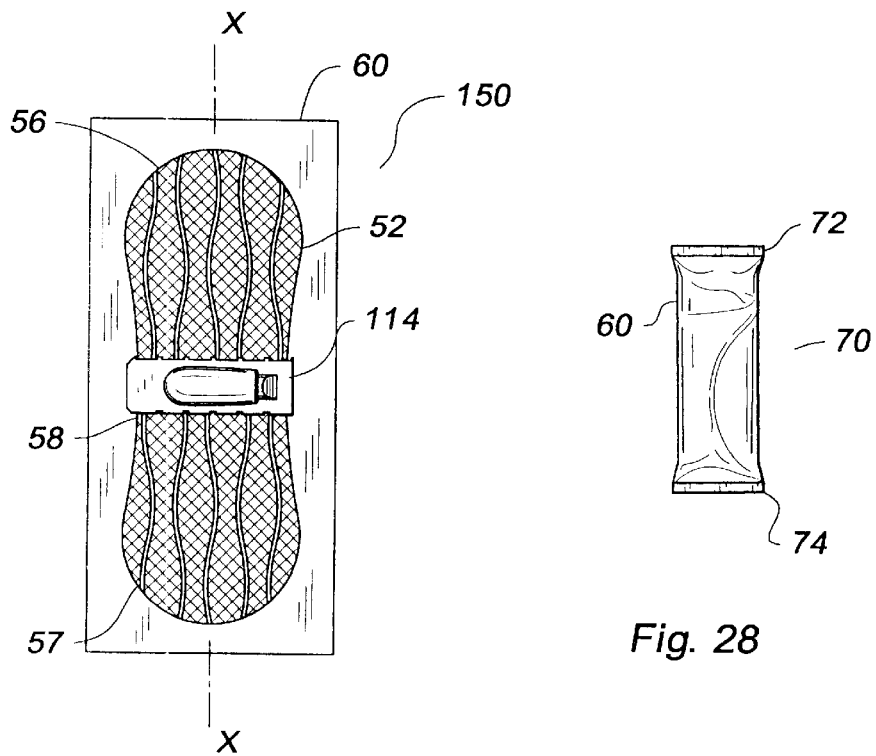
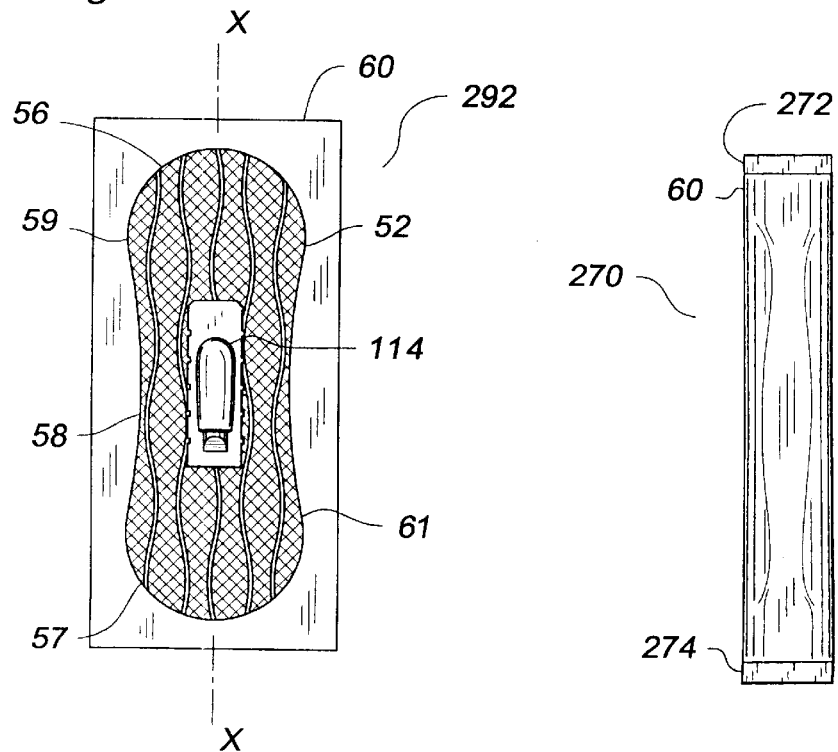
Fig. 27
Fig. 28
Fig. 29
Fig. 30

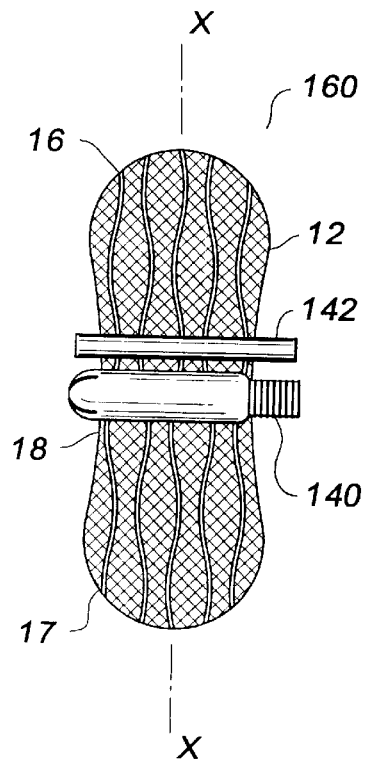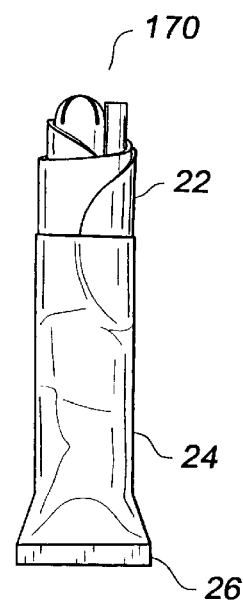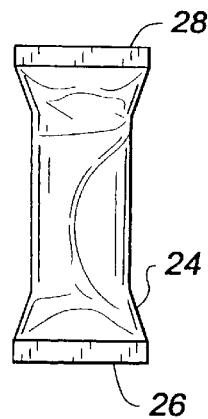
Fig. 31  Fig. 32  Fig. 33
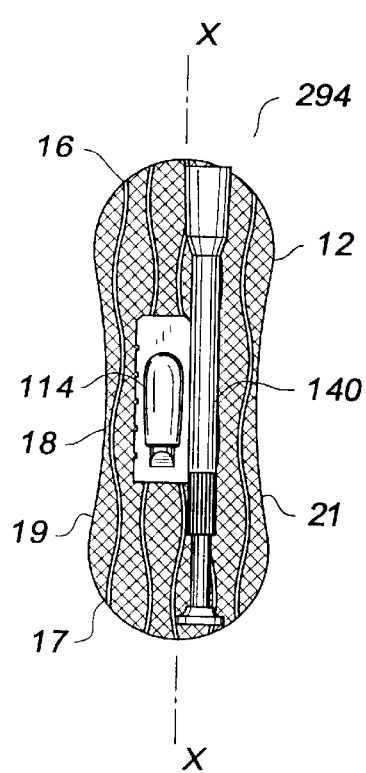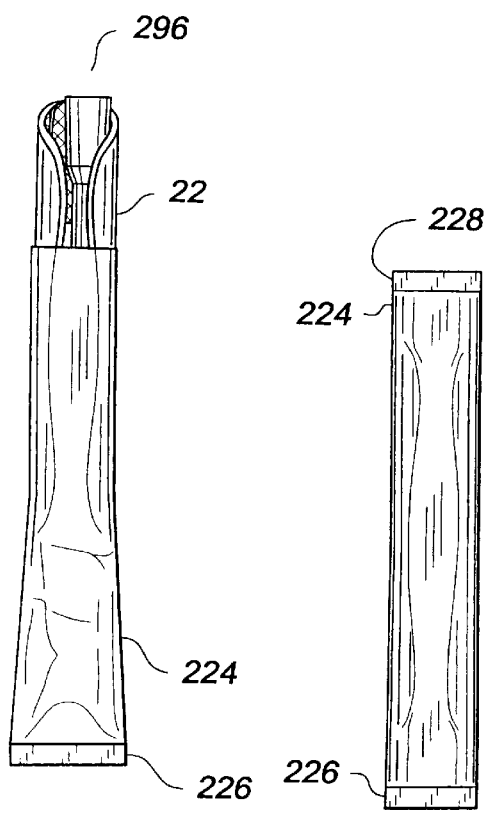
Fig. 34  Fig. 35  Fig. 36

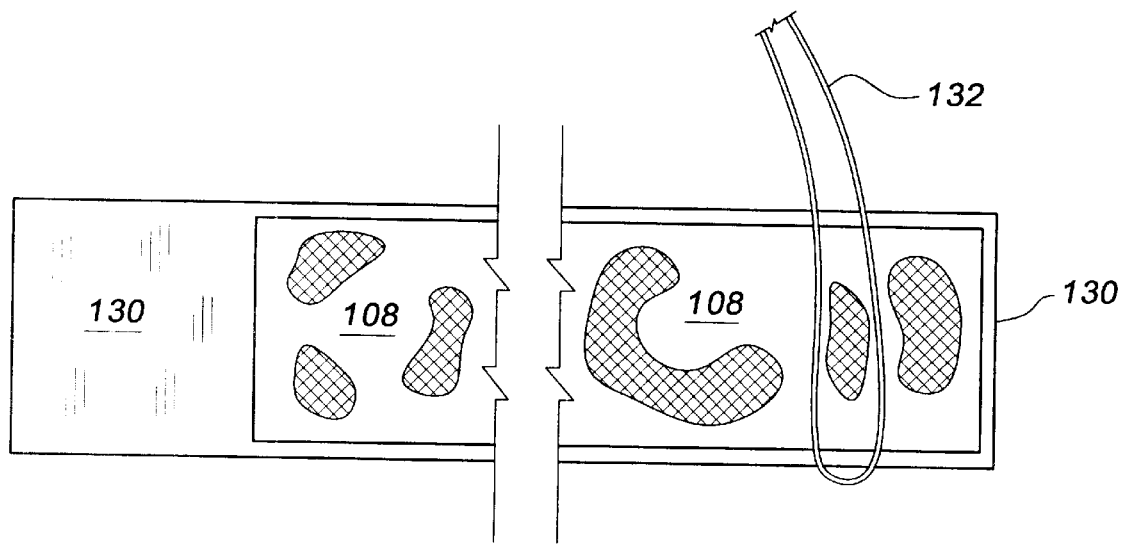
Fig. 45
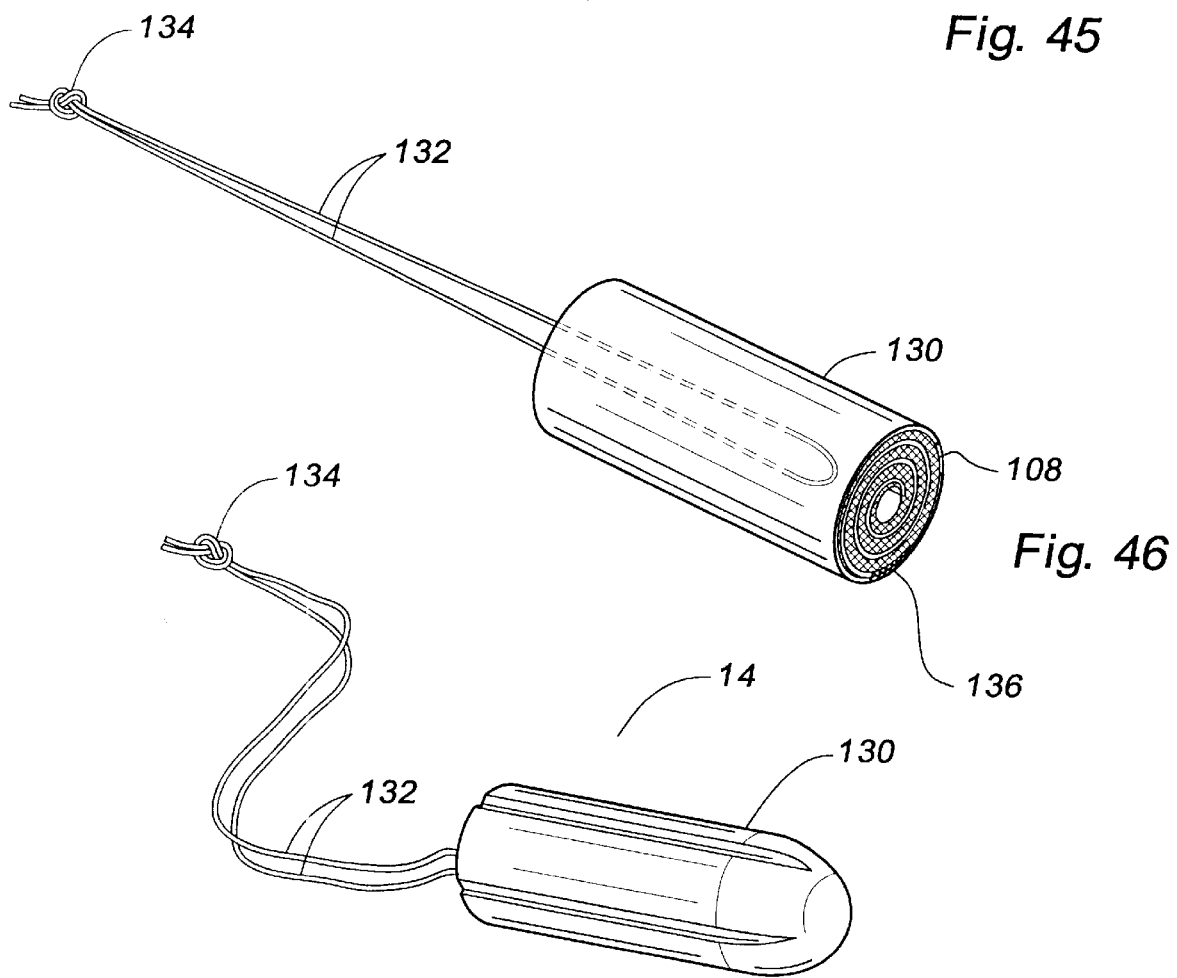
Fig. 46
Fig. 47

C-WRAPPED ABSORBENT PAD ARTICLE AND METHOD

This application is a continuation-in-part of U.S. patent application Ser. No. 08/993,024, filed Dec. 18, 1997, now U.S. Pat. No. 5,891,127, and U.S. patent application Ser. No. 08/993,025, filed Dec. 18, 1997, now U.S. Pat. No. 5,827,251.

BACKGROUND OF THE INVENTION

1. Technical Field

This invention relates to a feminine sanitary protection absorbent article and method designed to protect a user by absorbing or containing menstrual fluids and other body exudates. More specifically, this invention relates to novel feminine sanitary protection packaging which provides full and complete sanitary protection, ease in handling, convenience, and discretion in packaging appearance.

2. Background

Absorbent articles such as sanitary napkins are designed to absorb body fluids, including menses, and may come in different functional designs as grouped into categories. In one category, sanitary napkins are externally worn about the pudendal area and are designed primarily for heavy flow. Secondly, panty liners or panty shields are thin products externally worn about the pudendal area and are developed for light flow. Thirdly, tampons are designed to be positioned internally within the vagina.

INTRODUCTION TO THE INVENTION

Sanitary napkins, as viewed as a first category of several different functional designs for feminine sanitary protection, can have high absorptive capacity with either a thin or thick absorptive element. However, compressive forces of the wearer's thighs and pudendal region during any physical movement, such as walking, can cause the sanitary napkin to shift from an original position protecting the vulvar area. After a relatively short period of time, the sanitary napkin may move away from the vaginal orifice. The wearer's movement, particularly vigorous movement such as rapid walking or running, also can cause discomfort such as by rubbing or chafing in the sensitive vulvar area.

In addition to concerns of sanitary napkin movement and wearer discomfort, a concern of high degree of wearing awareness may be present. Some thick sanitary napkins have a high profile appearance when viewed through a wearer's outer garments. The sanitary napkins can be very apparent when worn with tight fitting clothing including slacks, body suits, swimming suits, or similarly thin or close fitting outer garments.

Panty liners or panty shields, as viewed as a second category of functional designs for feminine sanitary protection, have been developed for light or low menstrual flows. Some panty liners or panty shields have the same concerns associated with sanitary napkins although their thin profiles make them more flexible, less obtrusive in appearance, and generally more comfortable than the bulky sanitary napkins. However, the thin-profile panty liners or panty shields can have a drawback in the performance area of absorptive capacity.

Tampons, as viewed as a third category of feminine care devices, are worn internally within the vaginal canal to intercept body fluid. Sometimes tampons may not function completely to prevent leakage because radial expansion of the tampon within the vaginal canal does not form a perfect seal. Yet without such radial expansion and swelling of the tampon within the vaginal canal, the tampon does not serve as a completely reliable sanitary protection device.

U.S. Pat. No. 5,383,868, issued to Hyun, discloses a sanitary napkin for absorbing and collecting a woman's menstrual liquids. An absorbent pad is positioned against the woman's abdomen and the skin area between the thighs so as to overlie the vaginal opening. A porous absorbent plug extends from one face of the pad so as to be inserted into the woman's vagina. Menstrual blood and associated secretions flow through the porous plug into the pad for collection and safe retention. The Hyun sanitary napkin does not provide a portable and disposable means of carrying vaginal absorbents or suppositories with a panty liner. The Hyun sanitary napkin further does not allow for a woman to use an applicator and then dispose of it conveniently.

U.S. Pat. No. 5,579,916, issued to Manko, discloses a kit or case with hinged sections for carrying feminine hygiene materials. The case is made of a washable material such as canvas or vinyl and is closed by a zipper. The Manko kit suffers from the drawbacks of a lack of disposability and a lack of a preferred level of discretion.

U.S. Pat. No. 5,046,620, issued to Barabino, discloses a re-usable method of storing and removal of personal hygiene products ranging from tampons to cosmetics, similar to a pocket-book or purse. The Barabino purse kit suffers from the draw-backs of a lack of disposability and reusability and does not include tampon applicators with absorbents or suppositories and liners. The Barabino purse only provides a storage container.

U.S. Pat. No. 4,425,130, issued to DesMarais, discloses a compound sanitary napkin having a primary menstrual pad and a panty protector. The DesMarais primary menstrual pad and panty protector are joined at their corresponding ends. The DesMarais compound sanitary napkin does not provide a separate, loose device in each package.

A new feminine sanitary protection package is needed which provides full and complete sanitary protection, ease in handling, convenience, and discretion in packaging appearance.

It is an object of the present invention to provide an absorbent article feminine sanitary protection to absorb or contain menstrual fluids and other body exudates, including urine.

Another object of this invention is to provide feminine sanitary protection, which is comfortable, physically and psychologically to the user, to wear and to handle.

Still another object of the present invention is to provide feminine sanitary protection, which is capable of absorbing significant amounts of menses and other body exudates, while providing enhanced wearer comfort and a low profile of appearance when viewed through a wearer's outer garments.

It is a further object of the present invention to provide feminine sanitary protection which is capable of absorbing significant amounts of body fluid while providing enhanced protection against leakage through to a wearer's outer garments.

It is a further object of the present invention to provide feminine sanitary protection which provides full and complete sanitary protection, efficiencies in material and manufacturing costs, ease in consumer handling, convenience, and discretion in packaging appearance.

These and other objects and advantages of the present invention will become more apparent to those skilled in the art in view of the following detailed description and the accompanying drawings.

SUMMARY OF THE INVENTION

The packaging article and method of the present invention include feminine sanitary protection packaging having a vaginal insert device comprising a vaginal insert or insert applicator, a sanitary napkin or panty liner or shield configured to fit the pudendal region of a woman, the sanitary napkin or panty liner or shield being rolled or wrapped around the vaginal insert or insert applicator to form a rolled or wrapped combination sanitary napkin or panty liner or shield and vaginal insert or insert applicator. A pouch around the rolled or wrapped combination sanitary napkin or panty liner or shield and vaginal insert or insert applicator provides for transporting and disposing of the combination sanitary napkin or panty liner or shield and vaginal insert or insert applicator of the present invention.

In one aspect, the sanitary napkin is an ultrathin pad. In one aspect, the sanitary napkin is a maxipad.

In one aspect, the sanitary napkin or panty liner or shield is rolled laterally around the vaginal insert or insert applicator to form a laterally rolled combination sanitary napkin or panty liner and vaginal insert or insert applicator.

In one aspect, an ultrathin pad or panty liner or shield is C-wrapped around the vaginal insert or insert applicator to form a C-wrapped combination ultrathin pad or panty liner and vaginal insert or insert applicator.

In one aspect, the vaginal insert includes a tampon or a vaginal suppository. In one aspect, the vaginal insert applicator further includes a tampon applicator or a vaginal suppository applicator.

In another aspect, the pouch is sealed and optionally can be perforated on at least one closed end for ease in opening.

In still another aspect, the pouch is formed and sealed around the combination sanitary napkin or panty liner and vaginal insert or insert applicator, wherein the pouch is formed from the release strip of the sanitary napkin or panty liner.

BRIEF DESCRIPTION OF THE DRAWINGS

FIG. 1 is an elevation view of a laterally rolled feminine sanitary protection combination of the present invention including a panty liner and a tampon.

FIG. 2 is an elevation view of the laterally rolled feminine sanitary protection combination of a panty liner and a tampon partially inserted into a novel feminine sanitary protection package.

FIG. 3 is an elevation view of the novel laterally rolled feminine sanitary protection package of the present invention including a panty liner and a tampon combination.

FIG. 4 is an elevation view of a C-wrapped feminine sanitary protection combination of the present invention including a panty liner and a tampon.

FIG. 5 is an elevation view of the C-wrapped feminine sanitary protection combination of a panty liner and a tampon partially inserted into a novel feminine sanitary protection package.

FIG. 6 is an elevation view of the novel C-wrapped feminine sanitary protection package of the present invention including a panty liner and a tampon combination.

FIG. 7 is an elevation view of a laterally rolled feminine sanitary protection combination of the present invention including a panty liner and a tampon applicator.

FIG. 8 is an elevation view of the laterally rolled feminine sanitary protection combination including a panty liner and a tampon applicator partially inserted into a novel feminine sanitary protection package.

FIG. 9 is an elevation view of the novel laterally rolled feminine sanitary protection package of the present invention including a panty liner and a tampon applicator combination.

FIG. 10 is an elevation view of a C-wrapped feminine sanitary protection combination of the present invention including a panty liner and a tampon applicator.

FIG. 11 is an elevation view of the C-wrapped feminine sanitary protection combination including a panty liner and a tampon applicator partially inserted into a novel feminine sanitary protection package.

FIG. 12 is an elevation view of the novel C-wrapped feminine sanitary protection package of the present invention including a panty liner and a tampon applicator combination.

FIG. 13 is an elevation view of a laterally rolled feminine sanitary protection combination of the present invention including a panty liner and a tampon.

FIG. 14 is an elevation view of the novel laterally rolled feminine sanitary protection package of the present invention including a panty liner and a tampon combination.

FIG. 15 is an elevation view of a C-wrapped feminine sanitary protection combination of the present invention including a panty liner and a tampon.

FIG. 16 is an elevation view of the novel C-wrapped feminine sanitary protection package of the present invention including a panty liner and a tampon combination.

FIG. 21 is an elevation view of a laterally rolled feminine sanitary protection combination of the present invention including a panty liner and a medicinal vaginal insert.

FIG. 22 is an elevation view of the laterally rolled feminine sanitary protection combination including a panty liner and a medicinal vaginal insert partially inserted into a novel feminine sanitary protection package.

FIG. 23 is an elevation view of the novel laterally rolled feminine sanitary protection package of the present invention including a panty liner and a medicinal vaginal insert combination.

FIG. 24 is an elevation view of a C-wrapped feminine sanitary protection combination of the present invention including a panty liner and a medicinal vaginal insert.

FIG. 25 is an elevation view of the C-wrapped feminine sanitary protection combination including a panty liner and a medicinal vaginal insert partially inserted into a novel feminine sanitary protection package.

FIG. 26 is an elevation view of the novel C-wrapped feminine sanitary protection package of the present invention including a panty liner and a medicinal vaginal insert combination.

FIG. 27 is an elevation view of a laterally rolled feminine sanitary protection combination of the present invention including a panty liner and a medicinal vaginal insert.

FIG. 28 is an elevation view of the novel laterally rolled feminine sanitary protection package of the present invention including a panty liner and a medicinal vaginal insert combination.

FIG. 29 is an elevation view of a C-wrapped feminine sanitary protection combination of the present invention including a panty liner and a medicinal vaginal insert.

FIG. 30 is an elevation view of the novel C-wrapped feminine sanitary protection package of the present invention including a panty liner and a medicinal vaginal insert combination.

FIG. 31 is an elevation view of a laterally rolled feminine sanitary protection combination of the present invention including a panty liner and a medicinal vaginal insert applicator.

FIG. 32 is an elevation view of the laterally rolled feminine sanitary protection combination including a panty liner and a medicinal vaginal insert applicator partially inserted into a novel feminine sanitary protection package.

FIG. 33 is an elevation view of the novel laterally rolled feminine sanitary protection package of the present invention including a panty liner and a medicinal vaginal insert applicator combination.

FIG. 34 is an elevation view of a C-wrapped feminine sanitary protection combination of the present invention including a panty liner and a medicinal vaginal insert applicator.

FIG. 35 is an elevation view of the C-wrapped feminine sanitary protection combination including a panty liner and a medicinal vaginal insert applicator partially inserted into a novel feminine sanitary protection package.

FIG. 36 is an elevation view of the novel C-wrapped feminine sanitary protection package of the present invention including a panty liner and a medicinal vaginal insert applicator combination.

FIG. 45 is a plan view of the construction of a tampon component of the present invention.

FIG. 46 is a perspective view of an uncompressed tampon component of the present invention.

FIG. 47 is a perspective view of a tampon component of the present invention.

DETAILED DESCRIPTION OF THE PREFERRED EMBODIMENTS

Figure 17:
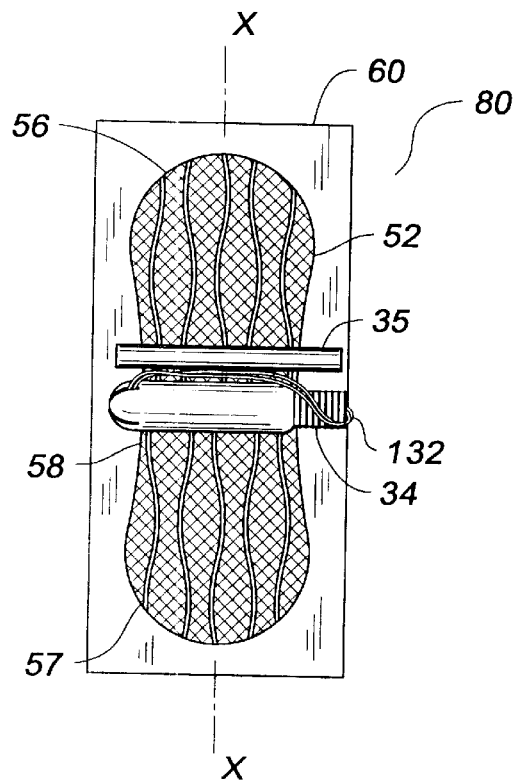
FIG. 17 is an elevation view of a laterally rolled feminine sanitary protection combination of the present invention including a panty liner and a tampon applicator.

Now, a novel feminine sanitary protection packaging and method have been developed which provide full and complete sanitary protection, efficiencies in material and manufacturing costs, ease in consumer handling, convenience, and discretion in packaging appearance.

The feminine sanitary protection packaging of the present invention provides a sanitary napkin or panty liner or shield combined around one or more vaginal inserts or vaginal insert applicators containing absorbents or medical devices for easy handling and use and easy disposal. In one aspect, the sanitary napkin or panty liner or shield is laterally rolled around a tampon. In one aspect, the sanitary napkin or panty liner or shield is laterally rolled around a medical device such as a medicinal suppository. In one aspect, an ultrathin pad or panty liner or shield is longitudinally C-wrapped around a tampon. In one aspect, the ultrathin pad or panty liner or shield is longitudinally C-wrapped around a medical device such as a medicinal suppository.

By sanitary napkin, it is meant an ultrathin pad or a maxipad as described in detail herein below.

By vaginal insertion device, it is meant a vaginal insert or vaginal insert applicator. By vaginal insert, it is meant a tampon or vaginal medicine insert such as a vaginal suppository. By vaginal insert applicator, it is meant a tampon applicator or a vaginal medicine insert applicator such as a vaginal suppository applicator.

The novel sanitary protection package fills a woman's need to have an absorbent pad or panty liner or shield readily accessible when using absorbent substances such as tampons or vaginal suppositories, e.g., such as for yeast infections. At the same time, the sanitary protection package of the present invention minimizes the use of superfluous materials, e.g., such as peel strip, extra packaging pouch, and the like.

The novel feminine sanitary protection packaging article and method provide a an absorbent pad or panty liner or shield laterally rolled or longitudinally C-wrapped around a separate plastic or paper applicator which contains substances such as absorbents, for menstrual use, or medications, e.g., such as for vaginal infections. The absorbent pad or panty liner or shield might also be laterally rolled or longitudinally C-wrapped directly around a device without an applicator.

In one aspect, the present invention includes a pouch component and the combination of an absorbent pad or a panty liner or shield partially surrounding one or more applicators containing absorbents or medical devices. The combination of the an absorbent pad or panty liner or shield around separate applicators containing absorbents or medical devices in one pouch provides a more discreet, convenient, and portable option than carrying the devices separately. The pouch, made with either biodegradable or non-biodegradable materials, serves to protect the adhesive element prior to wear and acts as a packaging agent for both products.

Sanitary napkins, also referred to as catamenial or feminine pads, and panty liners are described in Serbiak et al., U.S. No. Pat. 5,248,309; DiPalma et al., U.S. Pat. No. 5,649,916; and DiPalma et al., U.S. Pat. No. 5,609,588, which are hereby incorporated by reference and included herein as if they were repeated verbatim.

Sanitary napkins, also referred to as catamenial or feminine pads, are designed to be worn by a female to absorb medium to heavy flow of body fluids such as menses, blood, urine, and other excrements discharged by the body during a menstrual period. Sanitary napkins are external devices which are designed to be aligned approximate the pudendum region of the human body and are generally held in position by being adhesively or mechanically attached to an undergarment. Such products differ from tampons which are classified as internal devices and are designed to be physically inserted into the vaginal cavity.

Sanitary napkins include ultrathins and maxipads and differ from panty liners and panty shields in several noticeable ways. Sanitary napkins are generally larger in size, have a more defined three-dimensional configuration, are thicker in caliper, and are bulkier in appearance than panty liners or panty shields.

Functionally, sanitary napkins are different in that they are constructed to absorb a greater quantity of body fluid and are designed so that they can be worn for a longer period of time, for example, overnight, if needed.

Since sanitary napkins normally are used during the major discharge portion of a menstrual period, they are constructed to handle medium to heavy flows and commonly have a total absorbent capacity in the range of about 20 to 50 grams of fluid. Panty liners and panty shields, on the other hand, are designed to absorb relatively small amounts of body fluids and are marketed to be used at the beginning and end of a menstrual period when flow is light or spotty. Commercially available panty liners and panty shields are constructed to have a total absorbent capacity in the range of about 1 to 15 grams of fluid.

Panty liners or panty shields have a caliper of about 0.1 to 4 mm, as indicated in Table I. Ultrathin pads have a caliper of about 3–5 mm. Maxipads have a caliper of about 6 mm and higher. See Table I.

TABLE I

|  | Caliper | Absorbent Capacity |
| --- | --- | --- |
| Panty Liners | 0.1 to 4 mm | <1 to 15 grams of fluid |
| Ultrathin Pads | 3–5 mm | 20 to 50 grams |
| Maxipads | 6 mm + | 20 to 50 grams of fluid |

Absorbent Capacity Testing Method

The absorbent capacity of the sanitary napkin can be determined by the following test. In performing this test, one napkin is sufficient. The sanitary napkin to be tested first is conditioned by leaving it in a room which is at 21±1° C. and at 50±2% relative humidity for a period of two hours. If the napkin contains a peel strip, this is removed. The entire napkin, minus any peel strip, is weighed to the nearest 0.1 gram. The napkin is then submerged in a beaker of stabilized isotonic saline which contains no preservatives. A suitable sterile saline is commercially sold by Baxter Traven of Company of Deerfield, Ill. under catalog no. B3158-2. The napkin is submerged totally and is not bent or otherwise twisted or folded. The napkin is submerged for 10 minutes. The napkin is removed from the saline and suspended for two minutes in a vertical position to allow the saline to drain out of the napkin. The napkin then is placed with the body-side cover face down on an absorbent blotter. The blotter can be filter paper no. ED 631-25 available from the Ahlstrom Filtration Inc., Mount Holly Springs, Pa. 17065. A uniform 17.6 grams per square centimeter load is placed over the napkin to squeeze out excess fluid. The absorbent blotter is replaced every 30 seconds until the amount of fluid transferred to the absorbent blotter is less than 0.5 grams in a 30 second period. Next, the napkin is weighed to the nearest 0.1 gram, and the dry weight of the napkin is subtracted. The difference in grams is the capacity of the napkin.

The novel sanitary protection package combination of the present invention provides efficiencies in material and manufacturing costs and ease in consumer handling.

An advantage for such a packaging combination is that it conveniently contains all the products a women needs to feel fresh and completely protected, i.e., 100% protected, from stains on her undergarments or adjacent clothing. The novel sanitary protection package combination of the present invention provides women with an almost zero chance of experiencing staining on their undergarments when using these products together.

The product is more discreet and convenient than carrying two separate devices. A woman does not need to go out and buy two separate products, thereby saving money and time. Nor does she need to carry them around separately, and make sure when it comes time to use them that both separate packages still are available.

The packaging keeps them both fresh and protected from contamination.

In one aspect, the invention eliminates the need for a release strip on the adhesive-backed product since a sheet backing protects the adhesive element. The sheet also serves as a pouch which can be sealed together to enclose the combination panty liner and vaginal insert or insert applicator.

The novel feminine sanitary protection combination packaging provide a convenience of a discreet, convenient, portable system for carrying externally worn absorbent pads when using absorbent substances such as tampons or vaginal suppositories or vaginal creams, e.g., such as for yeast infections.

The pouch component of the present invention provides an individual pouch for transporting the combination of sanitary napkin or panty liner or shield laterally rolled or longitudinally C-wrapped around separate applicators containing absorbents or medical devices. The pouch keeps the combination package clean when kept and carried in a woman's purse and when it has been stored in the purse for awhile. The pouch component keeps the combination package sanitary in a purse, briefcase, backpack, car, or in a drawer.

The pouch component provides an individual pouch for disposing of the combination of the sanitary napkin or panty liner or panty shield and vaginal insert or insert applicator.

For attractive appearance, the individual pouch preferably is composed of a plastic material such as polyethylene or polypropylene, but may be composed of other materials, e.g., such as polyethylene oxide (PEO), polyvinyl alcohol (PVOH), polycaporolactone (PCL), paper, or a nonwoven material, e.g., such as spunbond/meltblown.

Referring now to the drawings, similar components in all of the drawings are referenced using the same identifying numerals.

Referring now to FIGS. 1–3, a sanitary protection device 10 includes a combination of a panty shield 12 and a tampon 14. The panty shield 12 has an hour glass shape, but may have an oval, straight, or race track shape, having a first end 16, a second end 17, and a middle 18. The panty shield 12 has a central longitudinal axis X—X. The tampon 14 is shown placed in a position near the middle 18 and is positioned transverse to the length of the device 10 and transverse to the longitudinal axis X—X of the panty shield 12. The combination of the panty shield 12 and the tampon 14 are rolled up by placing the tampon 14 near one end, i.e., either first end 16 or second end 17, and rolling the panty shield 12 laterally beginning with that end where the vaginal insert device of the tampon 14 is placed for rolling, to form a rolled combination 20. The rolled combination 20 is rolled in such a manner that a release strip backing 22 of the panty shield 12 is showing on the exterior of the rolled combination 20. The rolled combination 20 in the case of a panty liner and tampon combination typically will place the panty liner wrapped around the tampon to the extent of 720 degrees, by way of example. The rolled combination 20 is placed in a package 24 having a closed or sealed end 26. The package 24 can then be closed off at an opposite end 28. The package 24 can be closed at both ends 26 and 28 by ultrasonic sealing, heat sealing, adhesive, or embossing.

Referring now to FIGS. 4–6, a sanitary protection device 210 includes a combination of a panty liner 12 and a tampon 14. The panty liner 12 has an hour glass shape, but may have an oval, straight, or race track shape. The panty liner 12 has a first end 16, a second end 17, a middle section 18, a first side 19, and a second side 21. The panty liner 12 has a central longitudinal axis X—X. The tampon 14 is shown placed in a position near the middle section 18 and is positioned parallel to the length of the device 210 and coaxially aligned to the longitudinal axis X—X of the panty liner 12. The combination of the panty liner 12 and the tampon 14 are longitudinally C-wrapped up by placing the tampon 14 near one side, i.e., either first side 19 or second side 21, and C-wrapping the panty liner 12 longitudinally beginning with that side where the vaginal insert device of the tampon 14 is placed for C-wrapping, to form a longitudinally C-wrapped combination 220. The longitudinally C-wrapped combination 220 is longitudinally C-wrapped in such a manner that a release strip backing 22 of the panty liner 12 is showing on the exterior of the longitudinally C-wrapped combination 220. The longitudinally C-wrapped combination 220 in the case of a panty liner and tampon combination typically will place the panty liner wrapped around the tampon to the extent of 360 degrees, by way of example. The longitudinally C-wrapped combination 220 is placed in a package 224 having a closed or sealed end 226. The package 224 can then be closed off at an opposite end 228 as shown in FIG. 6. The package 224 can be closed at both ends 226 and 228 by ultrasonic sealing, heat sealing, adhesive, or embossing.

Referring now to FIGS. 7–9, a sanitary protection device 30 includes a combination of a panty shield 12 and a tampon applicator outer tube 34 and a plunger 35. A tampon having withdrawal string 132 is positioned in the outer tube 34, and the plunger 35 is designed to be inserted into the outer tube 34. The panty shield 12 has an oval, straight, race track, or hour glass shape with a first end 16, a second end 17, and a middle 18. The panty shield 12 has a central longitudinal axis X—X. The tampon applicator, consisting of an outside tube 34 and a plunger 35, is shown placed in a position near middle 18. Both the outside tube 34 and the plunger 35 are positioned transverse to the length of the device 30 and transverse to the longitudinal axis X—X of the panty shield 12. The combination of the panty shield 12 and the tampon applicator 34 and the plunger 35 are rolled up by placing the tampon applicator 34 and the plunger 35 near one end and rolling the panty shield 12 laterally beginning with that end where the vaginal insert device is placed for rolling, i.e., either the first end 16 or the second end 17, to form a rolled combination 40. The rolled combination 40 is rolled in such a manner that a release strip backing 22 of the panty shield 12 is showing on the exterior of the rolled combination 40. The rolled combination 40 is placed in a package 24 having a closed or sealed end 26. The package 24 then can be closed at the opposite end 28. The package 24 can be closed at both ends 26 and 28 by ultrasonic sealing, heat sealing, adhesive, or embossing. The package 24 can be made of a material preferably composed of a plastic material such as polyethylene or polypropylene, but may be composed of other materials, e.g., such as polyethylene oxide (PEO), polyvinyl alcohol (PVOH), polycaporolactone (PCL), paper, or a nonwoven material, e.g., such as spunbond/meltblown.

Referring now to FIGS. 10–12, a sanitary protection device 230 includes a combination of a panty liner 12 and a tampon applicator outer tube 34 and a plunger 35. A tampon having withdrawal string 132 is positioned in the outer tube 34, and the plunger 35 is designed to be telescopically moveable when it is inserted into the outer tube 34. The panty liner 12 has an oval, straight, race track, or hour glass shape with a first end 16, a second end 17, a middle section 18, a first side 19, and a second side 21. The panty liner 12 has a central longitudinal axis X—X. The tampon applicator, consisting of an outside tube 34 and a plunger 35, is shown placed in a position near central longitudinal axis X—X. Both the outside tube 34 and the plunger 35 are positioned parallel to the length of the device 230 and coaxially aligned with or parallel to the central longitudinal axis X—X of the panty liner 12. The combination of the panty liner 12 and the tampon applicator 34 and the plunger 35 are longitudinally C-wrapped up by placing the tampon applicator 34 and the plunger 35 near one side and C-wrapping the panty liner 12 longitudinally beginning with that side where the vaginal insert device is placed for C-wrapping, i.e., either the first side 19 or the second side 21, to form a longitudinally C-wrapped combination 240. The longitudinally C-wrapped combination 240 is longitudinally C-wrapped in such a manner that a release strip backing 22 of the panty liner 12 is showing on the exterior of the longitudinally C-wrapped combination 240. The longitudinally C-wrapped combination 240 is placed in a package 224 having a closed or sealed end 226. The package 224 then can be closed at the opposite end 228 as shown in FIG. 12. The package 224 can be closed at both ends 226 and 228 by ultrasonic sealing, heat sealing, adhesive, or embossing. The package 224 can be made of a material preferably composed of a plastic material such as polyethylene or polypropylene, but may be composed of other materials, e.g., such as polyethylene oxide (PEO), polyvinyl alcohol (PVOH), polycaporolactone (PCL), paper, or a nonwoven material, e.g., such as spunbond/meltblown.

Referring now to FIGS. 13 and 14, a sanitary protection device 50 includes a combination of a panty shield 52 and a tampon 14. The panty shield 52 can have an oval, straight, race track, or hour glass shape with a first end 56, a second end 57, and a middle 58. The panty shield 52 has a central longitudinal axis X—X. The panty liner 52 has a backing 60 composed of a material preferably composed of a plastic material such as polyethylene or polypropylene, but may be composed of other materials, e.g., such as polyethylene oxide (PEO), polyvinyl alcohol (PVOH), polycaporolactone (PCL), paper, or a nonwoven material, e.g., such as spunbond/meltblown.

The tampon 14 is shown placed in a position near the middle 58 and is positioned transverse to the length of the device 50 and the transverse central longitudinal axis X—X. The combination of the panty shield 52 and the tampon 14 is rolled up by placing the tampon 14 near one end and rolling the panty shield 52 laterally beginning with that end where the vaginal insert device is placed for rolling, i.e., either the first end 56 or the second end 57, to form a rolled combination panty shield and tampon to be placed in a pouch 70. The rolled combination pouch 70 is composed of a backing 60. The rolled combination pouch 70 has a closed end 72 and an opposite end 74. The rolled combination pouch 70 can be closed and sealed at both ends 72 and 74 after the tampon 14 is rolled up in the panty liner 52. The rolled combination pouch 70 can be closed and sealed at both ends 72 and 74 by ultrasonic sealing, heat sealing, adhesive, or embossing.

Referring now to FIGS. 15 and 16, a sanitary protection device 250 includes a combination of a panty liner 52 and a tampon 14. The panty liner 52 can have an oval, straight, race track, or hour glass shape with a first end 56, a second end 57, a middle section 58, a first side 59, and a second side 61. The panty liner 52 has a central longitudinal axis X—X. The panty liner 52 has a backing 60 composed of a material preferably composed of a plastic material such as polyethylene or polypropylene, but may be composed of other materials, e.g., such as polyethylene oxide (PEO), polyvinyl alcohol (PVOH), polycaporolactone (PCL), paper, or a nonwoven material, e.g., such as spunbond/meltblown.

The tampon 14 is shown placed in a position near the middle section 58 and is positioned parallel to the length of the device 250 and coaxially aligned with or parallel to the central longitudinal axis X—X. The combination of the panty liner 52 and the tampon 14 is longitudinally C-wrapped up by placing the tampon 14 near one side and C-wrapping the panty liner 52 longitudinally beginning with that side where the vaginal insert device is placed for C-wrapping, i.e., either the first side 59 or the second side 61, to form a longitudinally C-wrapped combination panty liner and tampon to be placed in a pouch 270. The longitudinally C-wrapped combination pouch 270 is composed of the backing 60. The longitudinally C-wrapped combination pouch 270 has a closed end 272 and an opposite end 274. The longitudinally C-wrapped combination pouch 270 can be closed and sealed at both ends 272 and 274 after the tampon 14 is longitudinally C-wrapped up in the panty liner 52. The longitudinally C-wrapped combination pouch 270 can be closed and sealed at both ends 272 and 274 by ultrasonic sealing, heat sealing, adhesive, or embossing.

The backing 60 protects the adhesive side of the panty liner 52 so that the adhesive remains clean prior to attachment of the panty shield 52 to the crotch of a wearer's panty. The backing 60 is oversize in the sense that it is a larger in dimension than the panty shield 52. The backing 60 can be a rectangle in shape having dimensions in the range of about 17–21 cm in length and about 6.5 to 10.5 cm in width as compared to a panty liner 52 having dimensions of about 16 cm length and about 5.5 cm width. Since the dimensions of the panty liner 52 can vary, the backing 60 can be a rectangle in shape having dimensions in the range of about 1–5 cm more in length and about 1 to 5 cm more in width than the panty liner 52. By oversize dimension, it is meant larger than the panty liner 52. The purpose of the oversize dimension of backing 60 is to provide for the packaging pouch component of the present invention.

The backing 60 protects the adhesive side of the panty liner 52 and eliminates the need for a release strip on the adhesive backed panty liner. The backing 60 can be a sheet which is sized to protect the adhesive element of the panty liner 52. The backing 60 also serves as a transporting and disposing pouch which is sealed to protect the cleanliness of the panty liner 52 and tampon 14.

The backing 60 is designed to serve as a releasable peel strip to be removed by the user prior to attachment of the absorbent article 52 to the inner crotch portion of her undergarment. The backing 60 serving as a releasable peel strip can be a white Kraft paper which is coated on one side so that it can be released readily from the adhesive side of the panty liner 52. The coating can be a silicone coating, such as a silicone polymer commercially available from Akrosil having an office located at 206 Garfield Avenue, Menasha, Wis. 54952.

The backing 60 can be composed of a material which is selected for its ability to be flushable or biodegradable.

Figure 18:
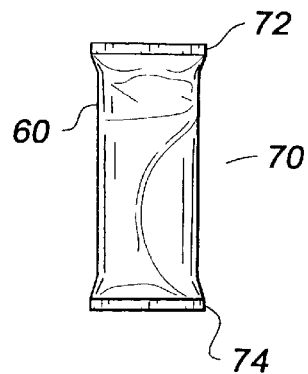
FIG. 18 is an elevation view of the novel laterally rolled feminine sanitary protection package of the present invention including a panty liner and a tampon applicator combination.

Referring now to FIGS. 17 and 18, a sanitary protection device 80 includes a combination of a panty shield 52, and a tampon applicator comprising an outer tube 34 and an inner tube 35. The outer tube 34 is designed to house an absorbent tampon. The inner tube 35 is designed to be telescopically slidable within the outer tube 34 so as to expel the tampon having withdrawal string 132 from an end of the outer tube 34 and position it into the vagina of a user.

The panty shield 52 can be an oval, race track, straight, or hour glass shape and has a first end 56, a second end 57, and a middle 58. The panty shield 52 has central longitudinal axis X—X. The panty liner 52 has a backing 60 which is larger in size dimension than the panty liner 52.

The tampon applicator outside tube 34 and the inner tube or plunger 35 are shown placed in a position near the middle 58 of the panty shield 52 and are positioned transverse to the length of the device 80 and transverse to the central longitudinal axis X—X. The combination of the panty shield 52 and the tampon applicator outside tube 34 and the plunger 35 are rolled up by placing the tampon applicator outside tube 34 and the plunger 35 near one end and rolling the panty shield 52 laterally beginning with that end where the vaginal insert device is placed for rolling, i.e., either the first end 56 or the second end 57, to form a rolled combination panty shield and tampon in the pouch 70. The rolled combination pouch 70 is composed of the backing 60. The rolled combination pouch 70 has a closed or sealed end 72 and closed or sealed opposite end 74. The rolled combination pouch 70 can be closed and sealed at both ends 72 and 74 by ultrasonic sealing, heat sealing, adhesive, or embossing.

Figure 19:
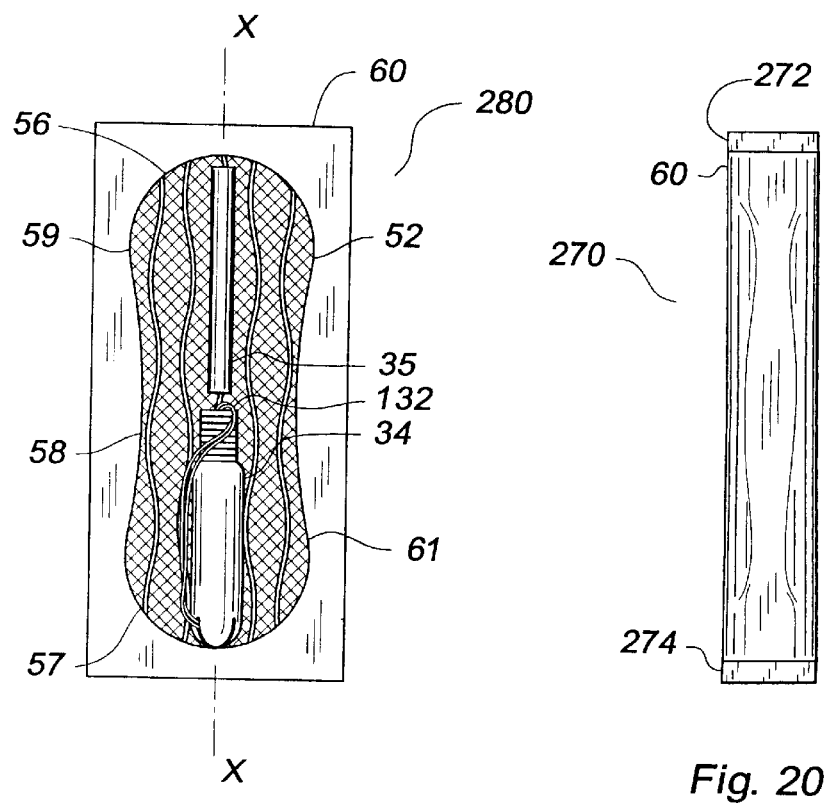
FIG. 19 is an elevation view of a C-wrapped feminine sanitary protection combination of the present invention including a panty liner and a tampon applicator.
Figure 20:
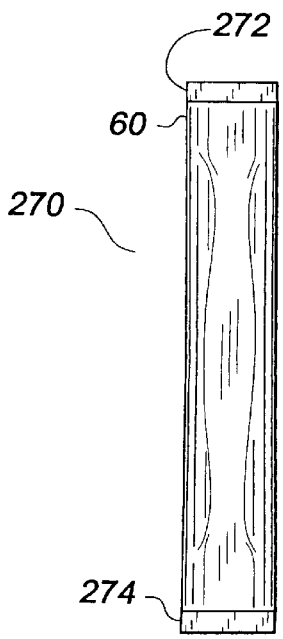
FIG. 20 is an elevation view of the novel C-wrapped feminine sanitary protection package of the present invention including a panty liner and a tampon applicator combination.

Referring now to FIGS. 19 and 20, a sanitary protection device 280 includes a combination of a panty liner 52, and a tampon applicator comprising an outer tube 34 and an inner tube 35. The outer tube 34 is designed to house an absorbent tampon. The inner tube 35 is designed to be telescopically slidable within the outer tube 34 so as to expel the tampon having withdrawal string 132 from an end of the outer tube 34 and position it into the vagina of a user.

The panty liner 52 can be an oval, race track, straight, or hour glass shape and has a first end 56, a second end 57, a middle section 58, a first side 59, and a second side 61. The panty liner 52 has central longitudinal axis X—X. The panty liner 52 has a backing 60 which is larger in size dimension than the panty liner 52.

The backing 60 protects the adhesive side of the panty liner 52 so that the adhesive is not contaminated prior to attachment to the crotch of a wearer's panty. The backing 60 is oversize in the sense that it is larger in dimension than the panty liner 52. The backing 60 can be a rectangle in shape having dimensions in the range of about 17–21 cm in length and about 6.5 to 10.5 cm in width as compared to a panty liner 52 having dimensions of about 16 cm length and about 5.5 cm width. Since the dimensions of the panty liner 52 can vary, the backing 60 can be a rectangle in shape having dimensions in the range of about 1–5 cm more in length and about 1 to 5 cm more in width than the panty liner 52. By oversize dimension, it is meant larger than the panty liner 52. The purpose of the oversize dimension of backing 60 is to provide for the packaging pouch component of the present invention.

The tampon applicator outside tube 34 and the inner tube or plunger 35 are shown placed in a position near the central longitudinal axis X—X of the panty liner 52 and are positioned parallel to the length of the device 280 and coaxially aligned with or parallel to the central longitudinal axis X—X. The combination of the panty liner 52 and the tampon applicator outside tube 34 and the plunger 35 are longitudinally C-wrapped up by placing the tampon applicator outside tube 34 and the plunger 35 near one side and C-wrapping the panty liner 52 longitudinally beginning with that side where the vaginal insert device is placed for C-wrapping, i.e., either the first side 59 or the second side 61, to form a longitudinally C-wrapped combination panty liner and tampon in the pouch 270. The longitudinally C-wrapped combination pouch 270 is composed of the backing 60. The longitudinally C-wrapped combination pouch 270 has a closed or sealed end 272 and closed or sealed opposite end 274. The longitudinally C-wrapped combination pouch 270 can be closed and sealed at both ends 272 and 274 by ultrasonic sealing, heat sealing, adhesive, or embossing.

Referring now to FIGS. 21–23, a sanitary protection device 110 includes a combination of a panty shield 12 and a vaginal suppository 114. The panty shield 12 can have an oval, straight, race track, or hour glass shape having a first end 16, a second end 17, and a middle 18. The panty shield 12 has a central longitudinal axis X—X. The vaginal suppository 114 is shown placed in a position near the middle 18 and is positioned transverse to the length of the device 110 and transverse to the longitudinal axis X—X of the panty shield 12. The combination of the panty shield 12 and the vaginal suppository 114 are rolled up by placing vaginal suppository 114 near one end and rolling the panty shield 12 laterally beginning with that end where the vaginal insert device is placed for rolling, i.e., either the first end 16 or the second end 17, to form a rolled combination 120. The rolled combination 120 is rolled in such a manner that a release strip backing 22 of the panty shield 12 is showing on the exterior of the rolled combination 120. The rolled combination 120 is placed in a package 24 having a closed end 26. The package 24 can then be closed at opposite end 28. The package 24 can be closed at both ends 26 and 28 by ultrasonic sealing, heat sealing, adhesive, or embossing.

Referring now to FIGS. 24–26, a sanitary protection device 260 includes a combination of a panty liner 12 and a vaginal suppository 114. The panty liner 12 can have an oval, straight, race track, or hour glass shape having a first end 16, a second end 17, a middle section 18, a first side 19, and a second side 21. The panty liner 12 has a central longitudinal axis X—X. The vaginal suppository 114 is shown placed in a position near the middle section 18 and is positioned parallel to the length of the device 260 and coaxially aligned with or parallel to the longitudinal axis X—X of the panty liner 12. The combination of the panty liner 12 and the vaginal suppository 114 are longitudinally C-wrapped up by placing vaginal suppository 114 near one side and C-wrapping the panty liner 12 longitudinally beginning with that side where the vaginal insert device is placed for C-wrapping, i.e., either the first side 19 or the second side 21, to form a longitudinally C-wrapped combination 290. The longitudinally C-wrapped combination 290 is longitudinally C-wrapped in such a manner that a release strip backing 22 of the panty liner 12 is showing on the exterior of the longitudinally C-wrapped combination 290. The longitudinally C-wrapped combination 290 is placed in a package 224 having a closed end 226. The package 224 can then be closed at opposite end 228. The package 224 can be closed at both ends 226 and 228 by ultrasonic sealing, heat sealing, adhesive, or embossing.

Referring now to FIGS. 27–28, a sanitary protection device 150 includes a combination of a panty shield 52 and a vaginal suppository 114. The panty shield 52 can have an oval, straight, race track, or hour glass shape having a first end 56, a second end 57, and a middle 58. The panty shield 52 has a central longitudinal axis X—X. The panty liner 52 has a backing 60.

The vaginal suppository 114 is shown placed in a position near the middle 58 and is positioned transverse to the length of the device 150 and transverse to the central longitudinal axis X—X. The combination of the panty shield 52 and the vaginal suppository 114 are rolled up by placing the vaginal suppository 114 near one end and rolling the panty shield 52 laterally beginning with that end where the vaginal insert device is placed for rolling, i.e., either a first end 56 or a second end 57, to form a rolled combination of the panty shield 52 and the vaginal suppository 114 in pouch 70. The rolled combination pouch 70 is composed of the backing 60. The rolled combination pouch 70 has closed or sealed end 72 and closed or sealed opposite end 74. The rolled combination pouch 70 can be closed and sealed at both ends 72 and 74 by ultrasonic sealing, heat sealing, adhesive, or embossing.

Referring now to FIGS. 29–30, a sanitary protection device 292 includes a combination of a panty liner 52 and a vaginal suppository 114. The panty liner 52 can have an oval, straight, race track, or hour glass shape having a first end 56, a second end 57, a middle section 58, a first side 59, and a second side 61. The panty liner 52 has a central longitudinal axis X—X. The panty liner 52 has a backing 60.

The vaginal suppository 114 is shown placed in a position near the middle section 58 and is positioned parallel to the length of the device 292 and coaxially aligned with or parallel to the central longitudinal axis X—X. The combination of the panty liner 52 and the vaginal suppository 114 are longitudinally C-wrapped up by placing the vaginal suppository 114 near one side and C-wrapping the panty liner 52 longitudinally beginning with that side where the vaginal insert device is placed for C-wrapping, i.e., either a first side 59 or a second side 61, to form a longitudinally C-wrapped combination of the panty liner 52 and the vaginal suppository 114 in pouch 270. The longitudinally C-wrapped combination pouch 270 is composed of the backing 60. The longitudinally C-wrapped combination pouch 270 has closed or sealed end 272 and closed or sealed opposite end 274. The longitudinally C-wrapped combination pouch 270 can be closed and sealed at both ends 272 and 274 by ultrasonic sealing, heat sealing, adhesive, or embossing.

Referring now to FIGS. 31–33, a sanitary protection device 160 includes a combination of a panty shield 12 and a vaginal suppository applicator outer tube 140 and inner tube 142. The vaginal suppository applicator outer tube 140 contains a medicinal suppository (not shown) to be positioned inside a body cavity of a woman. The panty shield 12 can have an oval, straight, race track, or hour glass shape having a first end 16, a second end 17, and a middle 18. The panty shield 12 has a central longitudinal axis X—X. The vaginal suppository applicator outer tube 140 and inner tube 142 is shown placed in a position near the middle 18 and is positioned transverse to the length of the device 160 and transverse to the longitudinal axis X—X of the panty shield 12. The combination of the panty shield 12 and the vaginal suppository applicator outer tube 140 and inner tube 142 are rolled up by placing vaginal suppository applicator outer tube 140 and inner tube 142 near one end and rolling the panty shield 12 laterally beginning with that end where the vaginal insert device is placed for rolling, i.e., either the first end 16 or the second end 17, to form a rolled combination 170. The rolled combination 170 is rolled in such a manner that a release strip backing 22 of the panty shield 12 is showing on the exterior of the rolled combination 170. The rolled combination 170 is placed in a package 24 having a closed end 26. The package 24 can then be closed at opposite end 28. The package 24 can be closed at both ends 26 and 28 by ultrasonic sealing, heat sealing, adhesive, or embossing.

Referring now to FIGS. 34–36, a sanitary protection device 294 includes a combination of a panty liner 12, a vaginal suppository 114, and a vaginal suppository applicator 140. The vaginal suppository applicator 140 is designed to position a medicinal suppository 114 inside a body cavity of a woman. The panty liner 12 can have an oval, straight, race track, or hour glass shape having a first end 16, a second end 17, a middle section 18, a first side 19, and a second side 21. The panty liner 12 has a central longitudinal axis X—X. The vaginal suppository applicator 140 and the vaginal suppository 114 are shown placed in a position near the middle section 18 and is positioned parallel to the length of the device 294 and coaxially aligned with or parallel to the longitudinal axis X—X of the panty liner 12. The combination of the panty liner 12 and the vaginal suppository applicator 140 are longitudinally C-wrapped up by placing vaginal suppository applicator 140 near one side and C-wrapping the panty liner 12 longitudinally beginning with that side where the vaginal insert device is placed for C-wrapping, i.e., either the first side 19 or the second side 21, to form a longitudinally C-wrapped combination 296. The longitudinally C-wrapped combination 296 is longitudinally C-wrapped in such a manner that a release strip backing 22 of the panty liner 12 is showing on the exterior of the longitudinally C-wrapped combination 296. The longitudinally C-wrapped combination 296 is placed in a package 224 having a closed end 226. The package 224 can then be closed at opposite end 228. The package 224 can be closed at both ends 226 and 228 by ultrasonic sealing, heat sealing, adhesive, or embossing.

Figure 37:
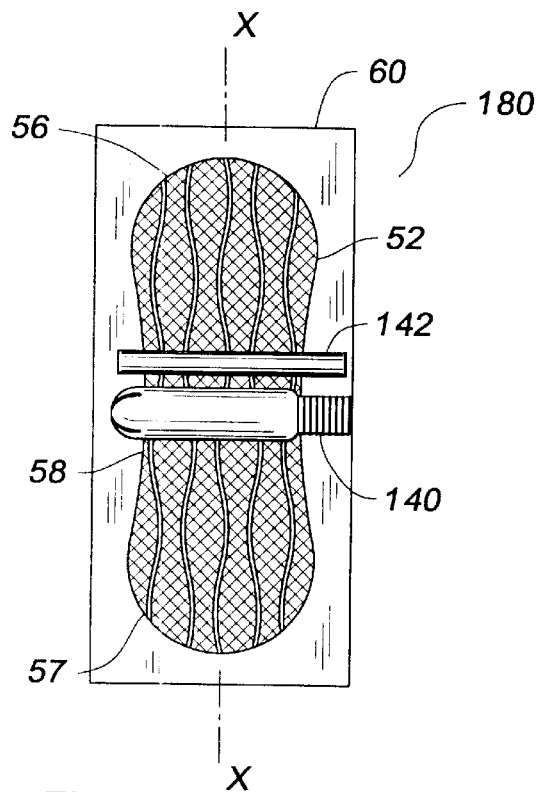
FIG. 37 is an elevation view of a laterally rolled feminine sanitary protection combination of the present invention including a panty liner and a medicinal vaginal insert applicator.
Figure 38:
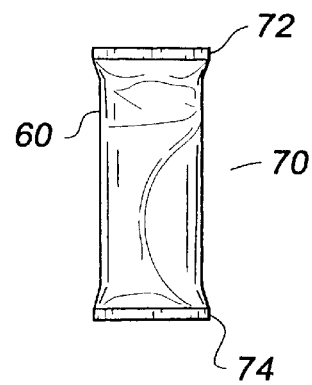
FIG. 38 is an elevation view of the novel laterally rolled feminine sanitary protection package of the present invention including a panty liner and a medicinal vaginal insert applicator combination.

Referring now to FIGS. 37–38, a sanitary protection device 180 includes a combination of a panty shield 52 and a vaginal suppository applicator outer tube 140 and inner tube 142. The vaginal suppository applicator 140 contains a medicinal suppository (not shown) to be positioned inside a body cavity of a woman. The panty shield 52 can have an oval, straight, race track, or hour glass shape having a first end 56, a second end 57, and a middle 58. The panty shield 52 has a central longitudinal axis X—X. The panty liner 52 has a backing 60.

The vaginal suppository applicator tubes 140 and 142 are shown placed in a position near the middle 58 and are positioned transverse to the length of the device 180 and transverse to the central longitudinal axis X—X. The combination of the panty shield 52 and the vaginal suppository applicator outer tube 140 and inner tube 142 are rolled up by placing the vaginal suppository applicator outer tube 140 and inner tube 142 near one end and rolling the panty shield 52 laterally beginning with that end where the vaginal insert device is placed for rolling, i.e., either a first end 56 or a second end 57, to form a rolled combination of the panty shield 52 and the vaginal suppository applicator outer tube 140 and inner tube 142 in pouch 70. The rolled combination pouch 70 is composed of the backing 60. The rolled combination pouch 70 has closed or sealed end 72 and closed or sealed opposite end 74. The rolled combination pouch 70 can be closed and sealed at both ends 72 and 74 by ultrasonic sealing, heat sealing, adhesive, or embossing.

Figure 39:
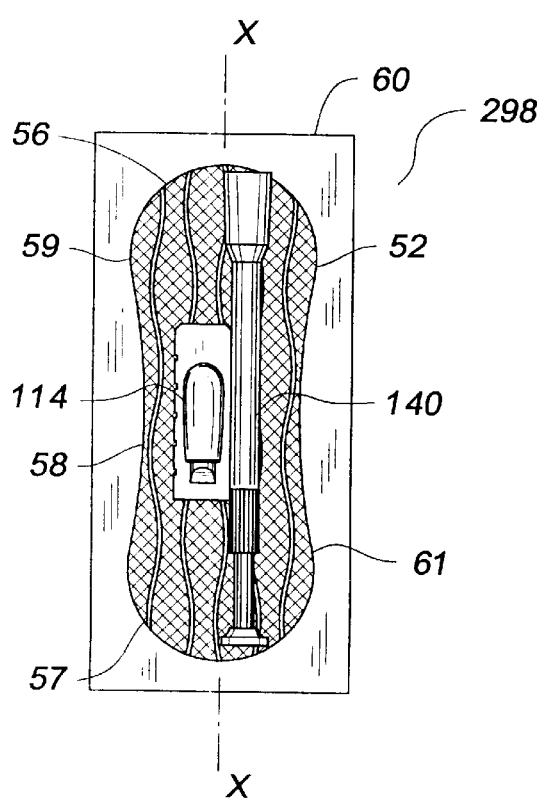
FIG. 39 is an elevation view of a C-wrapped feminine sanitary protection combination of the present invention including a panty liner and a medicinal vaginal insert applicator.
Figure 40:
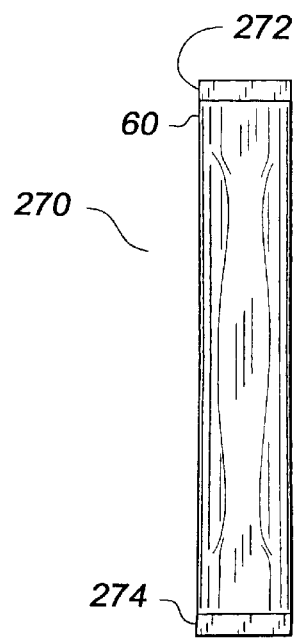
FIG. 40 is an elevation view of the novel C-wrapped feminine sanitary protection package of the present invention including a panty liner and a medicinal vaginal insert applicator combination.
Figure 41:
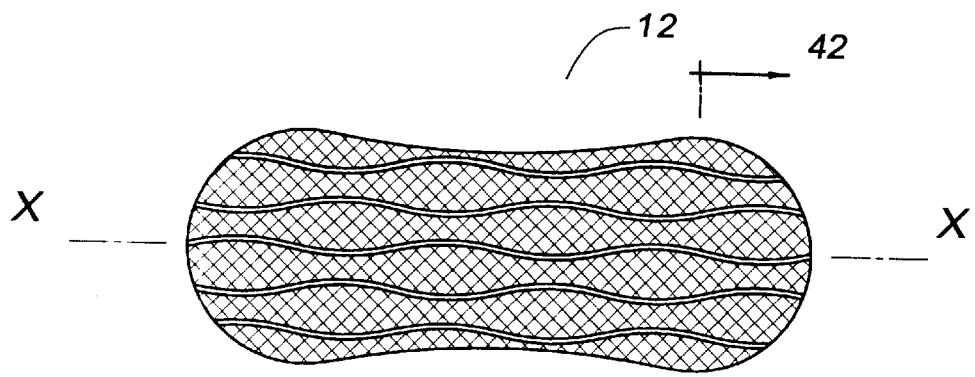
FIG. 41 is a plan view of a panty liner component of the present invention.
Figure 42:
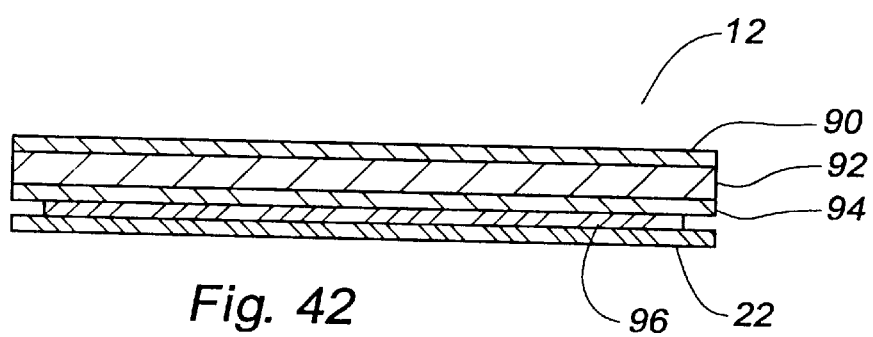
FIG. 42 is a cross sectional view, taken along line 42—42 of FIG. 41, of a panty liner component of the present invention.
Figure 43:
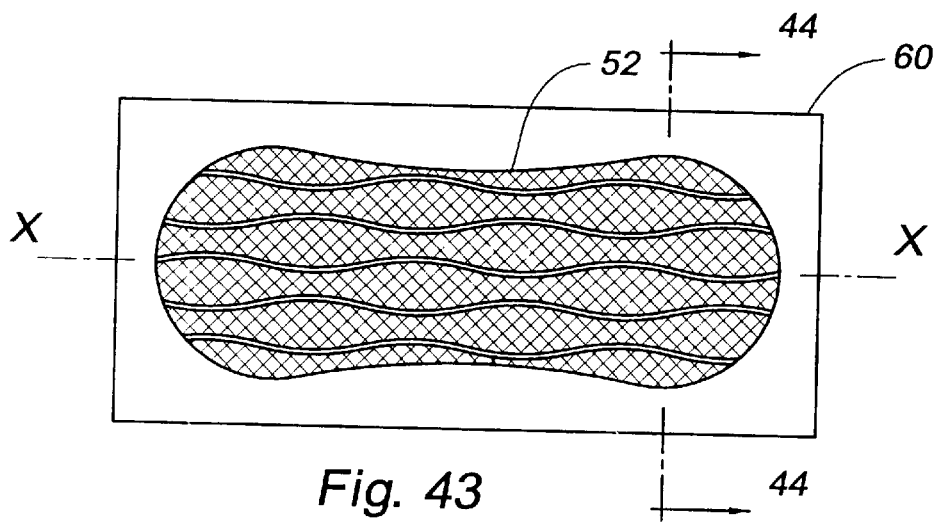
FIG. 43 is a plan view of a panty liner component of the present invention.
Figure 44:
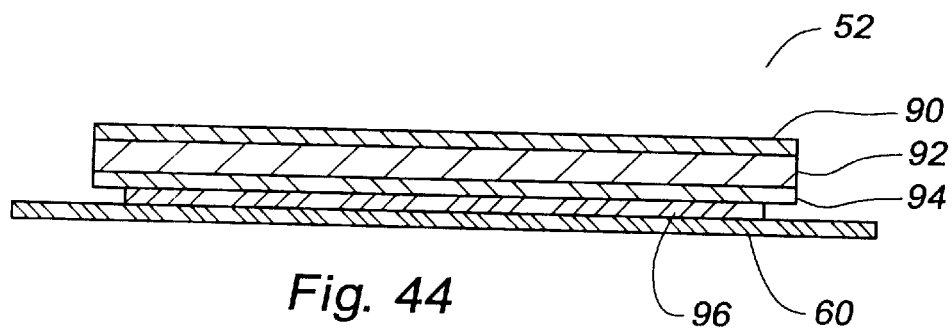
FIG. 44 is a cross sectional view, taken along line 44—44 of FIG. 43, of a panty liner component of the present invention.

Referring now to FIGS. 39–40, a sanitary protection device 298 includes a combination of a panty liner 52, a vaginal suppository 114, and a vaginal suppository applicator 140. The vaginal suppository applicator 140 is designed to position a medicinal suppository 114 inside a body cavity of a woman. The panty liner 52 can have an oval, straight, race track, or hour glass shape having a first end 56, a second end 57, a middle section 58, a first side 59, and a second side 61. The panty liner 52 has a central longitudinal axis X—X. The panty liner 52 has a backing 60.

The vaginal suppository 114 and vaginal suppository applicator 140 are shown placed in a position near the middle section 58 and is positioned parallel to the length of the device 292 and coaxially aligned with or parallel to the central longitudinal axis X—X. The combination of the panty liner 52 and the vaginal suppository applicator 140 are longitudinally C-wrapped up by placing the vaginal suppository applicator 140 near one side and C-wrapping the panty liner 52 longitudinally beginning with that side where the vaginal insert device is placed for C-wrapping, i.e., either a first side 59 or a second side 61, to form a longitudinally C-wrapped combination of the panty liner 52 and the vaginal suppository applicator 140 in pouch 270. The longitudinally C-wrapped combination pouch 270 is composed of the backing 60. The longitudinally C-wrapped combination pouch 270 has closed or sealed end 272 and closed or sealed opposite end 274. The longitudinally C-wrapped combination pouch 270 can be closed and sealed at both ends 272 and 274 by ultrasonic sealing, heat sealing, adhesive, or embossing.

Referring now to FIGS. 41–44, the panty shield 12 or 52 is shown which can be mass produced and packaged by the method of this invention. A plurality of identically shaped articles 12 or 52 can be manufactured by forming a sheet or web of absorbent material and then cutting or stamping out the articles 12 and 52. When forming a plurality of such articles 12 or 52 from paper, cardboard, or absorbent material, it may be advantageous to use a sheet or web of material consisting of a single layer. However, many absorbent pad articles 12 and 52, such as sanitary napkins, panty liners, or panty shields, are formed from multiple layers of different and distinct materials.

The absorbent pad articles 12 and 52 have an exterior profile in the shape of an hourglass and have a central longitudinal axis X—X. Absorbent pad articles 12 and 52 can have other shapes, e.g., such as a straight or rectangular shape, an oval shape, or a race track shape, designed to cover the pudendal region of a woman. Most absorbent articles 12 and 52 are longer than they are wide.

Such sanitary napkins, panty liners, and panty shields are designed for adhesive attachment to the crotch portion of an undergarment. These articles are normally constructed from several layers of different and distinct materials which are vertically arranged. Such layers, from top to bottom, can include a liquid-pervious cover 90, an absorbent 92, a liquid-impermeable baffle 94, an adhesive 96 secured to a lower surface of the baffle 94, and a removable release strip 22 (FIG. 22) and 60 (FIG. 23), respectively. Other layers, such as a transfer layer, a wicking layer, a layer containing super-absorbent materials, and additional absorbent layers can also be utilized.

The various layers can be vertically stacked, assembled, laminated, and/or bonded together to form the sheet or web of material from which the articles 12 and 52 are later cut or stamped out. The various layers can be bonded together by using heat, pressure, heat and pressure, adhesive, a hot melt glue, stitching with thread, ultrasonic bonding, mechanical bonding, thermal bonding, chemical bonding, or a combination of these and/or other means known to those skilled in the art.

The liquid-permeable cover 90 is designed to contact the body of the wearer and can be constructed of a woven or non-woven material which is easily penetrated by body fluid. The liquid-permeable cover 90 can also be formed from either natural or synthetic fibers. Suitable materials include bonded carded webs of polyester, polypropylene, polyethylene, nylon, or other heat-bondable fibers. Other polyolefins, such as copolymers of polypropylene and polyethylene, linear low-density polyethylene, finely-perforated film webs and net materials, also work well. A preferred material is a composite of an apertured thermoplastic film positioned above a non-woven fabric material. Such a composite material can be formed by extrusion of a polymer onto a web of spunbond material to form an integral sheet. One example of this material is an apertured, thermoplastic polyethylene film bonded to a spunbond material. Spunbond material is a non-woven material which is manufactured and commercially sold by Kimberly-Clark Corporation having an office located at 401 N. Lake Street, Neenah, Wis. 54956. The apertured film/non-woven laminate exhibits a smooth appearance and is soft to the touch. This material is soft and does not irritate the wearer's skin and yet has a cushioned feel because of its bulk. Another material useful as the liquid-permeable cover 90 is a spun-bond web of polypropylene. This spunbond web can contain from between about 1 percent to about 6 percent of a whitening agent, such as titanium dioxide ($TiO_2$) or calcium carbonate ($CaCO_3$) to give it a clean, white appearance. A uniform thickness of spunbond is desirable because it will have sufficient strength, after being perforated, to resist being torn or pulled apart during use. The most preferred polypropylene webs have a basis weight of between about 18 grams per square meter ($g/m^2$) to about 40 $g/M^2$. An optimum weight is between about 30 $g/m^2$ to about 40 $g/m^2$.

The absorbent layer 92 can be present as a single layer or as two or more distinct layers. The absorbent layer 92 can be formed from various natural or synthetic fibers such as wood pulp fibers, virgin cellulose fibers, regenerated cellulose fibers, cotton fibers, peat moss, or a blend of pulp and other fibers. The absorbent layer 92 also could be formed from a fine pore fabric such as wet-laid, air-dried tissue or from an uncreped through air-dried (UCTAD) tissue having a basis weight of from about 30 $g/m^2$ to about 120 $g/m^2$. The UCTAD tissue can be prepared by a process disclosed in U.S. Pat. No. 5,048,589 issued to Crook et al. on Sep. 17, 1991. The UCTAD tissue is disclosed in U.S. Pat. No. 5,399,412 issued to Sudall et al. on Mar. 21, 1995. Each of these patents is incorporated by reference and made a part hereof. The absorbent layer 92 also may be comprised of other well-known materials such as cellulose fibers, rayon fibers, cellulose sponge, hydrophilic synthetic sponge, for example polyurethane, and the like.

The liquid-impermeable baffle 94 is designed to permit the passage of air or vapor out of the absorbent articles 12 and 52 while blocking the passage of body fluid. The liquid-impermeable baffle 94 can be made from any material having these properties. The baffle 94 also can be constructed from a material that will block the passage of vapor as well as fluids, if desired. A good material from which the liquid-impermeable baffle 94 can be constructed is a micro-embossed, polymeric film, such as polyethylene or polypropylene. Bi-component films can also be used. A preferred material is polyethylene film. Most preferably, the polyethylene film will have a thickness in the range of from about 0.5 mm to about 2.0 mm.

It should be noted that construction adhesive can be used in the product to attach and bond the various layers together. For example, construction adhesive can be used to bond the liquid-impermeable baffle 94 to the absorbent 92 or to bond the absorbent 92 to the liquid-permeable cover 90. The presence of such construction adhesive and the amount used will depend upon manufacturing specifications. Useful construction adhesives are commercially sold by National Starch and Chemical Company, having an office located at 10 Finderne Ave., Bridgewater, N.J. 08807.

The absorbent articles 12 and 52 also include one or more elongated strips or areas of garment attachment adhesive 96 secured to the bottom surface of the liquid-permeable baffle 94. The garment attachment adhesive 96 functions to attach the absorbent articles 12 and 52 to the inner crotch portion of an undergarment during use. The garment attachment adhesive 96 enables the sanitary napkin or panty liner to be properly aligned and retained relative to the user's vaginal opening so that maximum fluid protection can be obtained. The garment attachment adhesive 96 can cover the complete bottom surface of the liquid-impermeable baffle 94 or only a portion of it. The garment attachment adhesive 96 can consist of a swirl pattern of adhesive or be one or more strips of adhesive. The garment attachment adhesive 96 also can consist of a plurality of adhesive dots which are randomly or uniformly arranged on the exterior surface of the baffle 94. When in strip form, the garment attachment adhesive 96 can be aligned along the central longitudinal axis X—X of the absorbent articles 12 and 52. Alternatively, the garment attachment adhesive 96 can be present as two or more spaced apart longitudinal strips. The garment attachment adhesive 96 is of such a nature that it will allow the user to remove the absorbent article 12 or 52 and reposition it on her undergarment if needed. A hot melt adhesive which works well as the garment attachment adhesive is commercially sold by National Starch and Chemical Company having an office located at 10 Finderne Avenue, Bridgewater, N.J. 08807.

In order to protect the garment attachment adhesive 96 from contamination prior to use, the adhesive 96 can be protected by a releasable peel strip 22 or 60. The releasable peel strip 22 or 60 can be a white Kraft paper which is coated on one side so that it can be released from the adhesive 96. The coating can be a silicone coating, such as a silicone polymer commercially available from Akrosil having an office located at 206 Garfield Avenue, Menasha, Wis. 54952. The release strips 22 and 60 are designed to be removed by the user prior to attachment of the absorbent articles 12 and 52, respectively, to the inner crotch portion of her undergarment.

Referring now to FIGS. 45–47, the construction of a catamenial tampon 14 component of the present invention is shown. The tampon 14 includes an absorbent 108 which has been compressed into a generally cylindrical shape and a liquid-permeable cover 130 which surrounds or encloses at least a portion of the absorbent 108. The tampon 14 can be constructed by positioning the absorbent 108 on the cover 130, as indicated in FIG. 45 and then rolling the two layers into a generally cylindrical shape. This uncompressed cylindrical shape, shown in FIG. 46, is known as a "softwind." The softwind is then compressed into a tampon "pledget" 14 as is shown in FIG. 47. It should be noted that it is also possible first to roll the absorbent 108 into a generally cylindrical shape and then wrap the liquid-permeable cover 130 around it. It also is possible to roll up and compress the absorbent 108 before wrapping it in the cover 130.

The tampon "pledget" as shown as the catamenial tampon 14 in FIG. 47 is an internal sanitary protection device used for absorbing menses, blood, and other body fluids. The tampon 14 is normally used during a woman's menstrual period to prevent leakage of menstrual fluid. The tampon 14 includes an absorbent material, such as cotton, rayon, cellulose wadding, synthetic sponge, cellulose fluff, synthetic fibers, or combinations thereof, which can be compressed into a generally cylindrical shape. The cylindrically shaped absorbent material is usually surrounded by a liquid-permeable cover. Catamenial tampons 14 are available in a variety of sizes and shapes so as to accommodate different size vaginal cavities. The tampons 14 are sufficiently compressed to retain their sizes and shapes under normal atmospheric conditions but are designed to expand readily when wetted by body fluid. For example, after a tampon 14 is inserted into a woman's vaginal tract and is contacted by body fluid, the compressed tampon 14 attempts to re-expand approximately to it's original uncompressed size. This structural change allows the tampon to fill the vaginal cavity and absorb body fluid thereby preventing leakage.

Referring to FIG. 47, the tampon 14 further includes a withdrawal string 132 which is secured to either the absorbent 108, the cover 130, or to both and provides a safe and reliable means by which the tampon 14 can be withdrawn from a woman's vagina after it has absorbed a certain amount of menstrual fluid. The withdrawal string 132 can be assembled with the softwind, as depicted in FIG. 46, or it can be attached to the compressed pledget, depending upon one's preference. In either case, the free end of the withdrawal string 132 is tied in a knot 134 to assure that it will not be separated from the pledget.

The absorbent 108 can be formed from absorbent fibers which are first assembled into an absorbent ribbon or sheet. Alternatively, the absorbent 108 can be formed from absorbent fibers which are assembled and compressed into a generally cylindrical configuration. The absorbent 108 is preferably formed from cellulosic fibers, such as cotton and rayon. The absorbent can be 100% cotton, 100% rayon, or a blend of both cotton and rayon. A ratio of from about 15% cotton and about 85% rayon works well. The particular blend of fibers can vary depending on one's preference.

The cotton fibers should have a staple length of between about 5 mm to about 20 mm. The fibers can be bleached if desired. Bleaching will make the fibers whiter in appearance. The cotton should generally have a fiber size of between about 150 to about 280 microns.

The rayon fibers should have a staple length of between about 20 mm to about 35 mm. The fibers can also be bleached if desired. The rayon fibers should have a denier of between about 25 to about 28. Denier is a unit of fineness of yarn based on a standard of 50 milligrams per 450 meters of yarn.

The absorbent 108, when formed from an absorbent ribbon, is constructed from a blend of rayon and cotton fibers in a process known to those skilled in the art as "carding." Depending upon the desired absorbency one desires in the finished tampon, the basis weight of the absorbent ribbon can vary. The U.S. Food and Drug Administration (FDA) has set absorbency standards for "regular," "super," and "super-plus" size tampons. In order to meet these standards for the three above-identified sizes, the absorbent ribbons are targeted to have basis weights of about 127 grams per square meter $(g/m^2)$, $170 \, g/m^{2'}$ and $230 \, g/m^2$, respectively. Typically, the carding process is controlled to produce an absorbent ribbon with a width of about 50 mm for a "regular" size tampon and a width of about 55 mm for both the "super" and "super-plus" size tampons. During the assembly process, one end of the rectangular absorbent ribbon having a length of about 300 mm is positioned over a portion of the cover 130. The two materials then are rolled up into a generally cylindrically shape. This rolling action will cause the absorbent 108 to be located on the interior and be surrounded by the cover 130. The cover 130 will surround the exterior surface of the softwind and can overlap upon itself, if desired. The cover 130 can be bonded, as indicated by numeral 136, to itself and/or to the absorbent ribbon 108 using heat, pressure, or a combination of heat and pressure. The softwind then is compressed into a finished tampon pledges 14. Preferably, the bonding 136 will occur during the compression step.

The cover 130 can be formed from woven or non-woven materials having a porous substrate. Woven materials include textile fabrics and non-woven materials include spunbond and bended carded webs. Both of these non-woven materials are commercially sold by Kimberly-Clark Corporation, 401 N. Lake Street, Neenah, Wis. 54956. Another non-woven material which can be used as the cover 130 is formed from 100 percent polyester fibers held tegether by a binder. This polyester fibers material is known as powder-bonded-carded web (PBCW) and also is available from Kimberly-Clark Corporation in Neenah, Wis.

The withdrawal string 132 can be constructed from various types of threads or ribbons. A thread made from 100 percent cotton fibers works well. The withdrawal string 132 normally has a length extending beyond one end of the tampon 14 from about 2 inches to about 8 inches (about 50.8 mm to about 203.2 mm), preferably from about 4 inches to about 6 inches (about 102 mm to about 152.4 mm), and most preferably, about 5 inches (127 mm). The withdrawal string 132 can be dyed and treated with an anti-wicking agent, such as wax, before being secured to the softwind or pledget to prevent it from wicking menstrual fluid. A dry, clean withdrawal string 132 is preferred by the user when she goes to remove the tampon 14.

Figure 48:
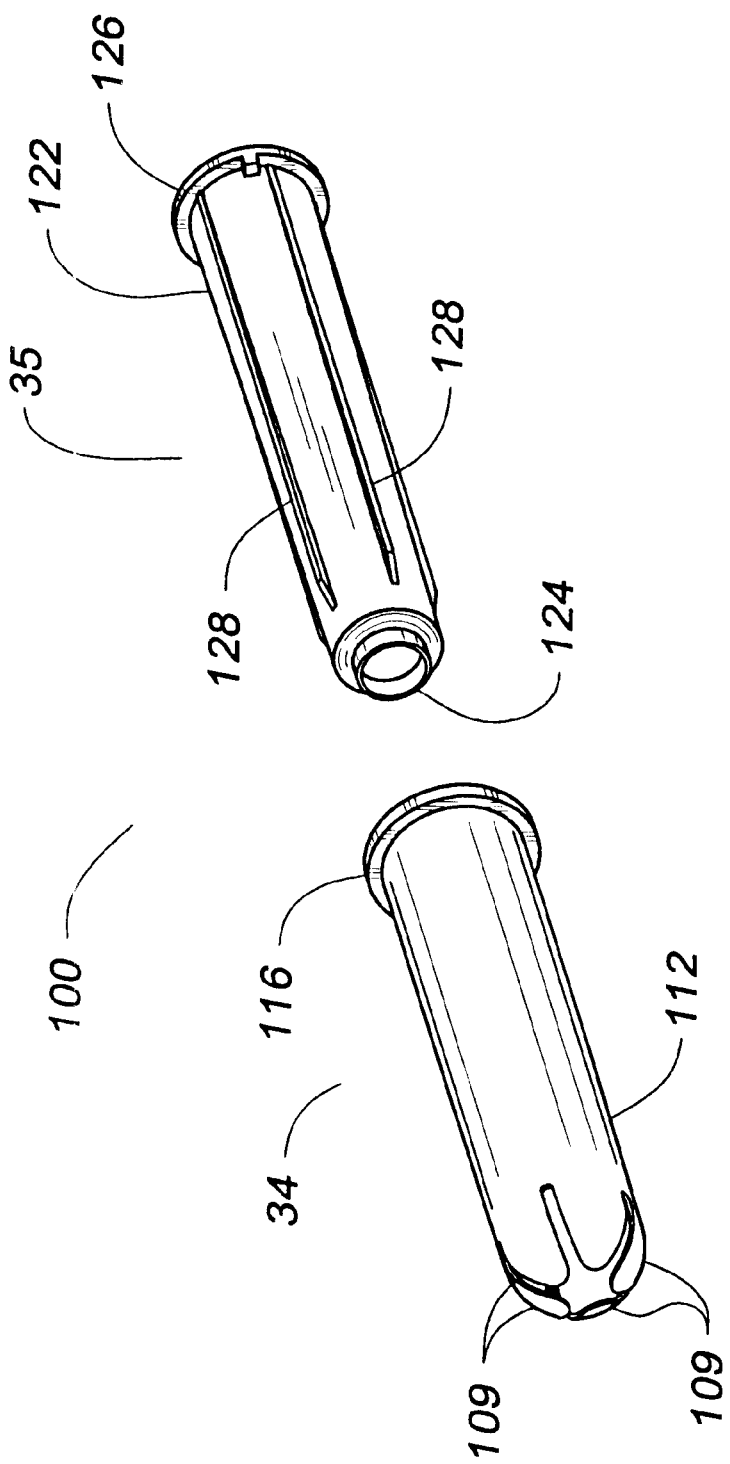
FIG. 48 is a perspective view of a tampon applicator component of the present invention.

Referring now to FIG. 48, the tampon applicator components of the present invention are constructed to provide a pair of elongated, concentric, telescoping tubes so that the outer tube can carry the tampon's absorbent material, the tampon's "pledget," while the inner tube serves as a plunger for dispensing the pledget.

The tampon applicator components for use in the packaging of the present invention are formed from either a plastic or paper. Plastic tampon applicators are preferred by many women because of a molded-in grip ring and a petal-shaped forward end which facilitates insertion of the applicator article while retaining and protecting the tampon while in the outer tube. Plastic tampon applicators typically are formed from polyethylene using injection molding.

A convenient place to dispose of a tampon applicator is in a toilet bowl. However, currently available commercial plastic applicators formed of polyethylene are ill-suited for such disposal. Presently available commercial plastic applicators of polyethylene will flush, but they settle in septic tanks without decomposing. They accumulate on screens in waste-water treatment plants, creating blockages. If the screens don't stop the applicator articles, they can escape into the environment intact, washing up on beaches. Plastic applicators don't always float so they can't be skimmed, and they don't settle to the bottom of settling tanks.

The novel feminine sanitary protection packaging of the present invention provides a solution for these problems in providing means for disposing of the tampon applicators without causing these problems.

Referring to FIG. 48, a tampon applicator 100 includes an outer tubular member 34 and a plunger 35. The outer tube 34 preferably is fabricated to include a one-piece main cylindrical body 112 extending into four or five flexible petal tips 109 disposed on the front end of the outer tube 34. A finger grip ring 116 is formed on the opposite end of the outer tube 34. The tampon applicator further includes the plunger 35 having a plunger body 122 adapted to serve as an inner tubular member. The plunger 35 has finger grip ring 126. The plunger 35 is designed to urge a pledget (not shown), housed in the hollow cylindrical body 112 of the outer tubular member 34, through the open petal tips 109 and further to insert the pledget into a woman's vagina. The insertion end 124 of the plunger 35 pushes against the tampon so as to expel it from the outer tube 34. The plunger 35 has structural guide ridges 128.

While the invention has been described in conjunction with several embodiments, it is to be understood that many alternatives, modifications, and variations will be apparent to those skilled in the art in light of the foregoing description. Accordingly, this invention is intended to embrace all such alternatives, modifications, and variations which fall within the spirit and scope of the appended claims.

We claim:

1. A feminine sanitary protection package, comprising:
   (a) a vaginal insertion device;
   (b) a panty liner or ultrathin pad configured to fit the pudendal region of a woman, said panty liner or ultrathin pad being C-wrapped longitudinally around said vaginal insertion device to form a longitudinally C-wrapped combination panty liner or ultrathin pad and vaginal insertion device; and
   (c) a pouch enclosing said longitudinally C-wrapped vaginal insertion device and panty liner or ultrathin pad combination, wherein said pouch provides means for transporting and disposing of said longitudinally C-wrapped combination.

2. The feminine sanitary protection package of claim 1 wherein said vaginal insertion device comprises a tampon.

3. The feminine sanitary protection package of claim 1 wherein said vaginal insertion device comprises a vaginal suppository.

4. The feminine sanitary protection package of claim 2 wherein said vaginal insertion device further comprises a tampon applicator.

5. The feminine sanitary protection package of claim 3 wherein said vaginal insertion device further comprises a vaginal suppository applicator.

6. The feminine sanitary protection package of claim 1 wherein said pouch provides a release strip for said panty liner or ultrathin pad.

7. The feminine sanitary protection package of claim 1 wherein said pouch is sealed.

8. The feminine sanitary protection package of claim 1 wherein said pouch is perforated on at least one closed end.

9. The feminine sanitary protection package of claim 1 wherein said pouch is composed of polyethylene.

10. A method for providing a feminine care sanitary protection package comprising the steps of:
    (a) providing a vaginal insertion device;
    (b) providing a panty liner or ultrathin pad configured to fit the pudendal region of a woman, said panty liner or ultra-thin pad being C-wrapped longitudinally around said vaginal insertion device to form a longitudinally C-wrapped combination panty liner or ultrathin pad and vaginal insertion device; and
    (c) providing a pouch around said longitudinally C-wrapped combination panty liner or ultrathin pad and insertion device, wherein said pouch provides means for transporting and disposing of said longitudinally C-wrapped combination panty liner or ultra-thin pad and vaginal insertion device.

11. The method for providing a feminine care sanitary protection package as set forth in claim 10 wherein said vaginal insertion device comprises a tampon.

12. The method for providing a feminine care sanitary protection package as set forth in claim 10 wherein said vaginal insertion device comprises a vaginal suppository.

13. The method for providing a feminine care sanitary protection package as set forth in claim 11 wherein said vaginal insertion device further comprises a tampon applicator.

14. The method for providing a feminine care sanitary protection package as set forth in claim 12 wherein said vaginal insertion device further comprises a vaginal suppository applicator.

15. The method for providing a feminine care sanitary protection package as set forth in claim 10 wherein said providing a pouch around said longitudinally C-wrapped combination panty liner or ultrathin pad and insertion device further comprises providing a release strip for said panty liner or ultra-thin pad.

16. A feminine sanitary protection package, comprising:
    (a) a vaginal insertion device;
    (b) a panty liner or ultrathin pad configured to fit the pudendal region of a woman, said panty liner or ultrathin pad being C-wrapped longitudinally around said vaginal insertion device to form a longitudinally C-wrapped combination panty liner or ultrathin pad and vaginal insertion device;
    (c) a release strip on said panty liner or ultrathin pad; and
    (d) a pouch positioned around said longitudinally C-wrapped vaginal insertion device and panty liner or ultrathin pad combination, wherein said pouch provides means for transporting and disposing of said longitudinally C-wrapped combination panty liner or ultrathin pad and vaginal insertion device, and further wherein said pouch is formed by said release strip on said panty liner or ultrathin pad.

17. The feminine sanitary protection package of claim 16 wherein said vaginal insertion device comprises a tampon.

18. The feminine sanitary protection package of claim 16 wherein said vaginal insertion device comprises a vaginal suppository.

19. The feminine sanitary protection package of claim 17 wherein said vaginal insertion device further comprises a tampon applicator.

20. The feminine sanitary protection package of claim 18 wherein said vaginal insertion device further comprises a vaginal suppository applicator.

* * * * *